United States Patent [19] [11] Patent Number: 4,789,702
Nunberg [45] Date of Patent: Dec. 6, 1988

[54] FELINE LEUKEMIA VIRUS VACCINE

[75] Inventor: Jack H. Nunberg, Oakland, Calif.

[73] Assignee: Cetus Corporation, Emeryville, Calif.

[21] Appl. No.: 873,681

[22] Filed: Jun. 12, 1986

Related U.S. Application Data

[60] Division of Ser. No. 612,003, May 18, 1984, Pat. No. 4,701,416, which is a continuation-in-part of Ser. No. 559,903, Dec. 9, 1983, abandoned.

[51] Int. Cl.$^4$ .................... C07K 7/08; A61K 39/12
[52] U.S. Cl. .................. 530/324; 530/327; 530/350; 530/402; 530/405; 530/806; 530/812; 530/820; 424/89; 424/88; 435/68; 435/70; 514/2; 514/14; 935/60; 935/109
[58] Field of Search ............. 424/89; 530/324, 327, 530/350, 402, 405, 806, 812, 820; 435/68, 70; 514/2, 14; 935/60, 109

[56] References Cited

U.S. PATENT DOCUMENTS

| 4,371,614 | 2/1983 | Anderson et al. | 435/68 |
| 4,406,885 | 9/1983 | Pinter | 424/88 |
| 4,434,157 | 2/1984 | Olsen | 424/89 |
| 4,499,188 | 2/1985 | Konrad et al. | 435/68 |
| 4,663,436 | 5/1987 | Elder et al. | 530/327 |

FOREIGN PATENT DOCUMENTS

| 30728 | 6/1981 | European Pat. Off. |
| 36776 | 9/1981 | European Pat. Off. |
| 105481 | 4/1984 | European Pat. Off. |
| 156299 | 10/1985 | European Pat. Off. |
| 173997 | 3/1986 | European Pat. Off. |
| WO84/04535 | 11/1984 | PCT Int'l Appl. |
| WO85/04871 | 11/1985 | PCT Int'l Appl. |

OTHER PUBLICATIONS

Sae et al., J. Virol., 46, 1983, pp. 829–840.
Mullins et al., N. A. Res., 8(15) 1980, pp. 3287–3305.
Mullins et al., J. Virol., 38, 1981, pp. 688–703.
Elder et al., J. Virol., 46, 1983, pp. 871–880.
Wunsch et al., EMBO, 2(12) 1983, pp. 2239–2246.
Weinstach et al., PNAS 80, 1983, pp. 4432–4436.
Kleid et al., Science, 214:1125–1128 (Dec. 4, 1981).
Emini et al., Nature, 304:699–703 (Aug. 25, 1983).
Nunberg et al., J. Virol., 49:629–632 (Feb., 1984).
Lewis et al., Inf. and Immun., 34 (3):888–894 (Dec., 1981).
Salerno et al., J. Natl. Cancer Inst., 61 (6):1487–1493 (Dec., 1978).
Rao et al., Gene, 7:79–82 (1979).
Bosselman et al., J. Virol., 44 (1):19–31 (Oct., 1982).
Wimmer et al., Nature, 308:19 (Mar. 1, 1984).
Meloen et al., J. Gen. Virol., 64:1193–1198 (1983).
Francis et al., Abstract entitled, "Priming with Peptides of Foot-and-Mouth Disease Virus (FMDV)" (for 1983 Meeting at Cold Spring Harbor).
Green et al., Cell, 28:477–487 (Mar., 1982).
Sherr et al., J. Virol., 34 (1):200–212 (Apr., 1980).
Bittle et al., Nature 298:30–33 (Jul. 1, 1982).
Moore et al. abstract entitled, "A Highly Antigenic Portion of FMDV O$_1$, VP$_1$ Elicits Bovine Antibodies Which Protect Mice but not Cattle from FMDV Infection".
Jarrett et al., The Veterinary Record, 101:304–305 (Oct. 8, 1977).
Noronha et al., Virology, 85:617–621 (1978).
Noronha et al., Nature, 267:54–56 (May 5, 1977).
Pedersen et al., manuscript submitted to ASM Publication Dept. and not accepted for publication as of Apr. 16, 1985.
Hopp et al., PNAS (USA), 78 (6):3824–3828 (Jun., 1981).
Chem. Abstracts, 81:316 (24077d) (1974).

Primary Examiner—John Kight
Assistant Examiner—Garnette D. Draper
Attorney, Agent, or Firm—Lisabeth F. Murphy; Thomas E. Ciotti; Albert P. Halluin

[57] ABSTRACT

Polypeptides that are synthesized or expressed directly in microorganisms, include an amino acid sequence that is homologous to at least a portion of gp70 envelope protein of FELV, and are immunogens that elicit or prime a humoral response in cats and immunize cats against FeLV infection. The microbially produced polypeptides are exemplified by a group of E. coli-expressed fusion proteins that comprise a portion of the trp leader peptide and a portion of the trp E protein fused to various portions of a subgroup B gp70 envelope protein. The synthesized polypeptides are exemplified by polypeptides that are homologous to segments of the hydrophilic domains of the gp70 protein.

13 Claims, 18 Drawing Sheets pKHR-1

(A. Roach, N. Davidson)

```
GA-FELV·env:
|signal peptide                      27                                            54
ATG GAA AGT CCA ACG CAC CCA AAA CCC TCT AAA GAT AAG ACT CTC TCG TGG AAC
 M   E   S   P   T   M   P   K   P   S   K   D   K   T   L   S   W   N
                                     81                          |gp70       108
TTA GTG TTT CTG GTG GGG ATC TTA TTC ACA ATA GAC ATA GGA ATG GCC AAT CCT
 L   V   F   L   V   G   I   L   F   T   I   D   I   G   M   A   N   P
                                    135                                       162
AGT CCG CAC CAA GTG TAT AAT GTA ACT TGG ACA ATA ACC AAC CTT GTA ACT GGA
 S   P   H   Q   V   Y   N   V   T   W   T   I   T   N   L   V   T   G
                                    189                                       216
ACA AAG GCT AAT GCC ACC TCC ATG TTG GGA ACC CTG ACA GAC GCC TTC CCT ACC
 T   K   A   N   A   T   S   M   L   G   T   L   T   D   A   F   P   T
                                    243                                       270
ATG TAT TTT GAC TTA TGT GAT ATA ATA GGA AAT ACA TGG AAC CCT TCA GAT CAG
 M   Y   F   D   L   C   D   I   I   G   N   T   W   N   P   S   D   Q
                                    297                                       324
GAA CCA TTC CCA GGG TAT GGA TGT GAT CAG CCT ATG AGG AGG TGG CAA CAG AGA
 E   P   F   P   G   Y   G   C   D   Q   P   M   R   R   W   Q   Q   R
                                    351                                       378
AAC ACA CCC TTT TAT GTC TGT CCA GGA CAT GCC AAC CGG AAG CAA TGT GGG GGG
 N   T   P   F   Y   V   C   P   G   H   A   N   R   K   Q   C   G   G
                                    405                                       432
CCA CAA GAT GGG TTC TGC GCT GTA TGG GGT TGC GAG ACC ACC GGG GAA ACC TAT
 P   Q   D   G   F   C   A   V   W   G   C   E   T   T   G   E   T   Y
                                    459                                       486
TGG AGA CCC ACC TCC TCA TGG GAC TAC ATC ACA GTA AAA AAA GGG GTT ACT CAG
 W   R   P   T   S   S   W   D   Y   I   T   V   K   K   G   V   T   Q
                                    513                                       540
GGA ATA TAT CAA TGT AGT GGA GGT GGT TGG TGT GGG CCC TGT TAC GAT AAA GCT
 G   I   Y   Q   C   S   G   G   G   W   C   G   P   C   Y   D   K   A
                                    567                                       594
GTT CAC TCC TCG ACA ACG GGA GCT AGT GAA GGG GGC CGG TGC AAC CCC TTG ATC
 V   H   S   S   T   T   G   A   S   E   G   G   R   C   N   P   L   I
                                    621                                       648
TTG CAA TTT ACC CAA AAG GGA AGA CAA ACA TCT TGG GAT GGA CCT AAG TCA TGG
 L   Q   F   T   Q   K   G   R   Q   T   S   W   D   G   P   K   S   W
                                    675                                       702
GGG CTA CGA CTA TAC CGT TCA GGA TAT GAC CCT ATA GCC CTG TTC TCG GTA TCC
 G   L   R   L   Y   R   S   G   Y   D   P   I   A   L   F   S   V   S
                                    729                                       756
CGG CAA GTA ATG ACC ATT ACG CCG CCT CAG GCC ATG GGA CCA AAT CTA GTC CTG
 R   Q   V   M   T   I   T   P   P   Q   A   M   G   P   N   L   V   L
                                    783                                       810
CCT GAT CAA AAA CCC CCA TCC AGG CAA TCT CAA ATA GAG TCC CGA GTA ACA CCT
 P   D   Q   K   P   P   S   R   Q   S   Q   I   E   S   R   V   T   P
                                    837                                       864
CAC CAT TCC CAA GGC AAC GGA GGC ACC CCA GGT ATA ACT CTT GTT AAT GCC TCC
 H   H   S   Q   G   N   G   G   T   P   G   I   T   L   V   N   A   S
                                    891                                       919
ATT GCC CCT CTA AGT ACC CCT GTC ACC CCC GCA AGT CCC AAA CGG ATT GGG ACC
 I   A   P   L   S   T   P   V   T   P   A   S   P   K   R   I   G   T
                                    945                                       972
GGA GAT AGG TTA ATA AAT TTA GTA CAA GGG ACA TAC CTA GCC TTA AAT GCC ACC
 G   D   R   L   I   N   L   V   Q   G   T   Y   L   A   L   N   A   T
                                    999                                      1026
GAC CCC AAC AGA ACT AAA GAC TGT TGG CTC TGC CTG GTT TCT CGA CCA CCC TAT
 D   P   N   R   T   K   D   C   W   L   C   L   V   S   R   P   P   Y
```

```
                                            1053                                                    1080
TAC GAA GGG ATT GCA ATC TTA GGT AAC TAC AGC AAC CAA ACA AAC CCC CCC CCA
 Y   E   G   I   A   I   L   G   N   Y   S   N   Q   T   N   P   P   P
                               1107                                                 1134
TCC TGC CTA TCT ATT CCG CAA CAC AAA CTA ACC ATA TCT GAA GTA TCA GGG CAA
 S   C   L   S   I   P   Q   H   K   L   T   I   S   E   V   S   G   Q
                                       1161                                         1188
GGA CTG TGC ATA GGG ACT GTT CCT AAG ACC CAC CAG GCT TTG TGC AAT GAG ACA
 G   L   C   I   G   T   V   P   K   T   H   Q   A   L   C   N   E   T
                                       1215                                         1242
CAA CAG GGA CAT ACA GGG GCG CAC TAT CTA GCC GCC CCC AAT GGC ACC TAT TGG
 Q   Q   G   H   T   G   A   H   Y   L   A   A   P   N   G   T   Y   W
                               1269                                                 1296
GCC TGT AAC ACT GGA CTC ACC CCA TGT ATT TCC ATG GCG GTG CTC AAT TGG ACC
 A   C   N   T   G   L   T   P   C   I   S   M   A   V   L   N   W   T
                                       1323                                         1350
TCT GAT TTT TGT GTC TTA ATC GAA TTA TGG CCC AGA GTG ACT TAC CAT CAA CCC
 S   D   F   C   V   L   I   E   L   W   P   R   V   T   Y   H   Q   P
                               1377                                          p15e   1404
GAA TAT GTG TAC ACA CAT TTT GCC AAA GCT GCC AGG TTC CGA AGA GAA CCA ATA
 E   Y   V   Y   T   H   F   A   K   A   A   R   F   R   R   E   P   I
                                       1431                                         1458
TCA CTA ACT GTT GCC CTC ATG TTG GGA GGA CTC ACT GTA GGG GGC ATA GCC GCG
 S   L   T   V   A   L   M   L   G   G   L   T   V   G   G   I   A   A
                               1485                                                 1512
GGG GTC GGA ACA GGG ACT AAA GCC CTC ATT GAA ACA GCC CAG TTC AGA CAA CTA
 G   V   G   T   G   T   K   A   L   I   E   T   A   Q   F   R   Q   L
                                       1539                                         1566
CAA ATG GCC ATG CAC ACA GAC ATC CAG GCC CTA GAA GAG TCA ATT AGT GCC TTA
 Q   M   A   M   H   T   D   I   Q   A   L   E   E   S   I   S   A   L
                                       1593                                         1620
GAA AAG TCC CTG ACC TCC CTT TCT GAA GTA GTC TTA CAA AAC AGA CGG GGC CTG
 E   K   S   L   T   S   L   S   E   V   V   L   Q   N   R   R   G   L
                               1647                                                 1674
GAT ATT CTA TTC TTA CAA GAG GGA GGG CTC TGT GCC GCA TTA AAA GAA GAA TGT
 D   I   L   F   L   Q   E   G   G   L   C   A   A   L   K   E   E   C
                                       1701                                         1728
TGC TTC TAT GCG GAT CAC ACC GGA CTT GTC CGA GAC AAT ATG GCT AAA TTA AGA
 C   F   Y   A   D   H   T   G   L   V   R   D   N   M   A   K   L   R
                               1755                                                 1782
GAA AGA CTA AAA CAG CGG CAA CAA CTG TTT GAC TCC CAA CAG GGA TGG TTT GAA
 E   R   L   K   Q   R   Q   Q   L   F   D   S   Q   Q   G   W   F   E
                                       1809                                         1836
GGA TGG TTC AAC AAG TCC CCC TGG TTT ACA ACC CTA ATT TCC TCC ATT ATG GGC
 G   W   F   N   K   S   P   W   F   T   T   L   I   S   S   I   M   G
                               1863                                                 1890
CCC TTA CTA ATC CTA CTC CTA ATT CTC CTC TTC GGC CCA TGC ATC CTT AAC AGA
 P   L   L   I   L   L   L   I   L   L   F   G   P   C   I   L   N   R
                                       1917                                         1944
TTA GTA CAA TTC GTA AAA GAC AGA ATA TCT GTG GTA CAA GCC TTA ATT TTA ACC
 L   V   Q   F   V   K   D   R   I   S   V   V   Q   A   L   I   L   T
                               1971                                                 1998
CAA CAG TAC CAA CAG ATA AAG CAA TAC GAT CCG GAC CGA CCA TAA TTT CCA ATT
 Q   Q   Y   Q   Q   I   K   Q   Y   D   P   D   R   P
 $
```

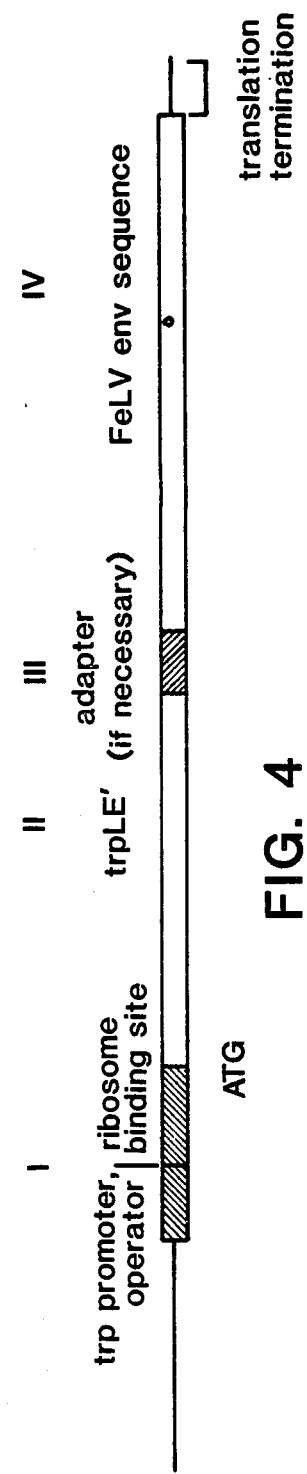

trpLE'-FeLV gp70 JUNCTION IN ptGA

... GCA CAG GAA TTC CCG GCC AAT CCT AGT ...
... ala  gln  glu  phe  pro  ala  asn  pro  ser ...

TRP LE'

```
|PvuII    10          20          30          40          50          60          70
CTGTGGTGTC ATGGTCGGTG ATCGCTAGGG TGCCGAGCGC ATCTCGACTG CACGGTGCAC CAATGCTTCT
            80          90         100         110         120         130         140
GGCGTCAGGT AGTTATTGGA AAGCTGTGGT ATGGCTGTGC AGGTCGTAAA TCACTGCATA ACTCGCTGCT
           150         160         170         180         190         200         210
GCCTAAGGCG CACTCCCGTT CTGGATAATG TTTTTTGCGC CGACATCATA ACGGTTCTGG CAAATATTCT
           220         230         240         250         260         270         280
GAAATGAGCT GTTGACAATT AATCATCGAA CTAGTTAACT AGTACGCAAG TTCACGTAAA AAGGGTATCG
                       298                             313                       328
ACA ATG AAA GCA ATT TTC GTA CTG AAA GGT TCA CTG GAC AGA GAT CTC GAC AGC
    M   K   A   I   F   V   L   K   G   S   L   D   R   D   L   D   S
            343                     358                     373               388
CGT ATT GAA CTG GAA ATG CGT ACC GAT CAT AAA GAG CTG TCT GAA CAT CTG ATG
R   I   E   L   E   M   R   T   D   H   K   E   L   S   E   H   L   M
                    403                     418                 433
CTG GTT GAT CTC GCC CGT AAT GAT CTG GCA CGC ATT TGC ACC CCC GGC AGC CGC
L   V   D   L   A   R   N   D   L   A   R   I   C   T   P   G   S   R
        448                     463                     478             493
TAC GTC GCC GAT CTC ACC AAA GTT GAC CGT TAT TCC TAT GTG ATG CAC CTC GTC
Y   V   A   D   L   T   K   V   D   R   Y   S   Y   V   M   H   L   V
                508                     523                 538
TCT CGC GTA GTC GGC GAA CTG CGT CAC GAT CTT GAC GCC CTG CAC GCT TAT CGC
S   R   V   V   G   E   L   R   H   D   L   D   A   L   H   A   Y   R
553                     568                     583                 598
GCC TGT ATG AAT ATG GGG ACG TTA AGC GGT GCG CCG AAA GTA CGC GCT ATG CAG
A   C   M   N   M   G   T   L   S   G   A   P   K   V   R   A   M   Q
            613                     628                     643               658
TTA ATT GCC GAG GCG GAA GGT CGT CGC CGC GGC AGC TAC GGC GGC GCG GTA GGT
L   I   A   E   A   E   G   R   R   R   G   S   Y   G   G   A   V   G
                    673                     688                 703
TAT TTC ACC GCG CAT GGC GAT CTC GAC ACC TGC ATT GTG ATC CGC TCG GCG CTG
Y   F   T   A   H   G   D   L   D   T   C   I   V   I   R   S   A   L
        718                     733                     748             763
GTG GAA AAC GGT ATC GCC ACC GTG CAA GCG GGT GCT GGT GTA GTC CTT GAT TCT
V   E   N   G   I   A   T   V   Q   A   G   A   G   V   V   L   D   S
                778                     793                 808
GTT CCG CAG TCG GAA GCC GAC GAA ACC CGT AAC AAA GCC CGC GCT GTA CTG CGC
V   P   Q   S   E   A   D   E   T   R   N   K   A   R   A   V   L   R
823                     838                     |EcoRI
GCT ATT GCC ACC GCG CAT CAT GCA CAG GAA TTC
A   I   A   T   A   H   H   A   Q   E   F
```

FIG. 7 ptGA Δ Bal I–Hind III (4.9kb)

ptGA Δ Bal I–Hin dIII

Ava I
partial Eco RI
Klenow repair
isolate (4.2kb)
religate ptGA- Ava I (4.2kb)

FELINE LEUKEMIA VIRUS VACCINE

CROSS-REFERENCE TO RELATED APPLICATION

This application is a divisional of application Ser. No. 612,003, filed May 18, 1984, now U.S. Pat. No. 4,701,416 which is a continuation-in-part of application Serial No. 559,903 filed Dec. 9, 1983, now abandoned.

DESCRIPTION

1. Technical Field

This invention is in the fields of protein chemistry, recombinant DNA technology, and immunoprevention of viral diseases. More particularly, it relates to novel proteins that are useful as feline leukemia virus (FeLV) vaccines.

2. Background Art

FeLV

FeLVs are a group of contagious oncogenic RNA viruses that cause both neoplastic and non-neoplastic diseases in cats. FeLV infections are the main cause of disease-related deaths in cats. During FeLV replication, a DNA copy of the viral RNA genome is made and inserted into the DNA of infected cells. The integrated FeLV DNA codes for the replication of more virus which is shed from infected cells. By recombining with the host's genes to generate feline sarcoma virus (FeSV), the virus can cause cell transformation.

The FLV genome is a 60–70S single stranded RNA consisting of a gag gene that encodes the internal viral proteins, a pol gene that codes for the viral RNA dependent DNA polymerase (reverse transcriptase), and an env gene that encodes the viral envelope proteins gp70 and p15E. Viral interference and neutralization tests have shown that there are three subgroups of envelope antigens (designated A, B and C) that are similar but distinct from each other and give rise to the three recognized FeLV subgroups (also designated A, B and C).

The fate of a cat that is exposed to FeLV will depend upon its immune response to the FeLV—particularly to the FeLV envelope antigens. Studies have shown that about 40% of the exposed population produce high titers of anti-FeLV envelope antibodies and become immune, about 30% do not respond adequately and become persistently infected, and about 30% are neither infected nor immunized but remain susceptible. The fact that a significant portion of the exposed population acquires natural immunity has led investigators to try a variety of materials as vaccines against FeLV. Inactivated virus was found to be ineffective except at high doses. Purified gp70 was also reported to be generally ineffective as a vaccine. Killed tumor cells have been reported to be successful in preventing leukemia but not viremia. A soluble tumor cell antigen obtained from the tissue culture medium of an FeLV transformed cell line (FL-74) was also tried and found effective in preventing the induction of FeLV virus infection.

Microbially Produced Vaccines

Science (1981) 214:1125–1128 and British patent application GB 2103622 A describe microbially-produced polypeptides that are useful as foot-and-mouth disease (FMDV) vaccines. Complementary DNA (cDNA) fragments were prepared from the portion of the FMDV genome that codes for the capsid protein VP3. These cDNA inserts were incorporated into a bacterial plasmid containing a tryptophan (trp) promoter and the recombinant plasmid was used to transform competent E. coli. The recombinant bacteria expressed a fusion protein composed of a polypeptide encoded by the trp leader and a portion of the trp E gene and a polypeptide encoded by the VP3 insert. The fusion protein was purified and tested in vitro and in vivo for its ability to bind anti-VP3 antibodies and its ability to prevent FMDV infection in livestock. Science (1981) 219:614–620 describes the synthesis of a surface protein of rabies virus via expression in recombinant E. coli of a gene derived from the rabies virus genome.

Vaccination Procedure

Emini, et al, Nature (1981) 304:699–703 report that a low subinfectious and subprotective dose of live poliovirus can be used to potentiate the immune response to synthetic peptides derived from poliovirus. It appears as if the initial synthetic vaccine "primes" the immune system and that the subsequent viral boost allows the initially-primed immune response to manifest itself in a potent humoral response. Other investigators have reported similar findings using microbially produced (recombinant) vaccines. These include poliovirus and hepatitis B (prime with recombinant/boost with live virus) and foot-and-mouth disease virus (prime with recombinant/boost with killed virus).

DISCLOSURE OF THE INVENTION

The present invention concerns polypeptides that comprise an amino acid sequence that defines an antigenic determinant of FeLV and that are useful as immunogens for eliciting or priming a humoral response in cats and immunizing cats against FeLV infection. These polypeptides may be made by (1) direct expression in microorganisms of recombinant DNA that includes an FeLV env DNA sequence that codes for such an amino acid sequence or (2) conventional polypeptide synthesis procedures in the case of small polypeptides. The immunogenic properties of these polypeptides are unexpected since the prior art reports that purified gp70 protein was not an effective FeLV vaccine.

The microbially produced polypeptides of the invention comprise an amino acid sequence that is homologous to at least a portion of the amino acid sequence of gp70 envelope protein of FeLV and are immunogens that elicit or prime a humoral response in cats and immunize cats against FeLV infection. One group of such polypeptides are E. coli-produced fusion proteins comprising a portion of the trp leader peptide and a portion of the trp E protein fused to a portion of the gp70 envelope protein of feline leukemia virus that defines an antigenic determinant. Polypeptides of this group were made by isolating fragments of the env gene from available molecularly cloned FeLV DNA sequences, or synthesizing env gene fragments, incorporating the fragments into a replicable plasmid that uses the E. coli trp LE' sequence to direct expression of E. coli with the plasmid, and growing the resulting transformants in an appropriate bacterial culture medium. The polypeptide may be worked up from the E. coli cells by lysing the cells, removing E. coli endotoxins from the lysate, and reducing the lysate with a reducing agent that cleaves disulfide bonds. It may be desirable to subsequently reoxidize the material.

Portions of the gp70 protein that have been identified as being immunogenic may be synthesized by standard polypeptide synthesis techniques and coupled to a carrier protein to produce effective FeLV immunogens.

The polypeptide or polypeptide-carrier protein conjugate is combined with an appropriate adjuvant and a parenteral vehicle for use as a vaccine. Cats may be immunized against FeLV by administering immunogenic amounts of these vaccines to the cats parenterally. They are preferably employed to prime an immune response and are followed with boosts of killed virus or subinfectious amounts of live virus.

BRIEF DESCRIPTION OF THE DRAWINGS

In the drawings:

FIG. 4 is a diagram of the structure of the expression system for the trp LE'-FeLV fusion proteins described in the examples.

FIG. 7 is the nucleotide sequence that codes for the trpLE' polypeptide and the deduced amino acid sequence of that polypeptide.

MODES FOR CARRYING OUT THE INVENTION

Figure 1:
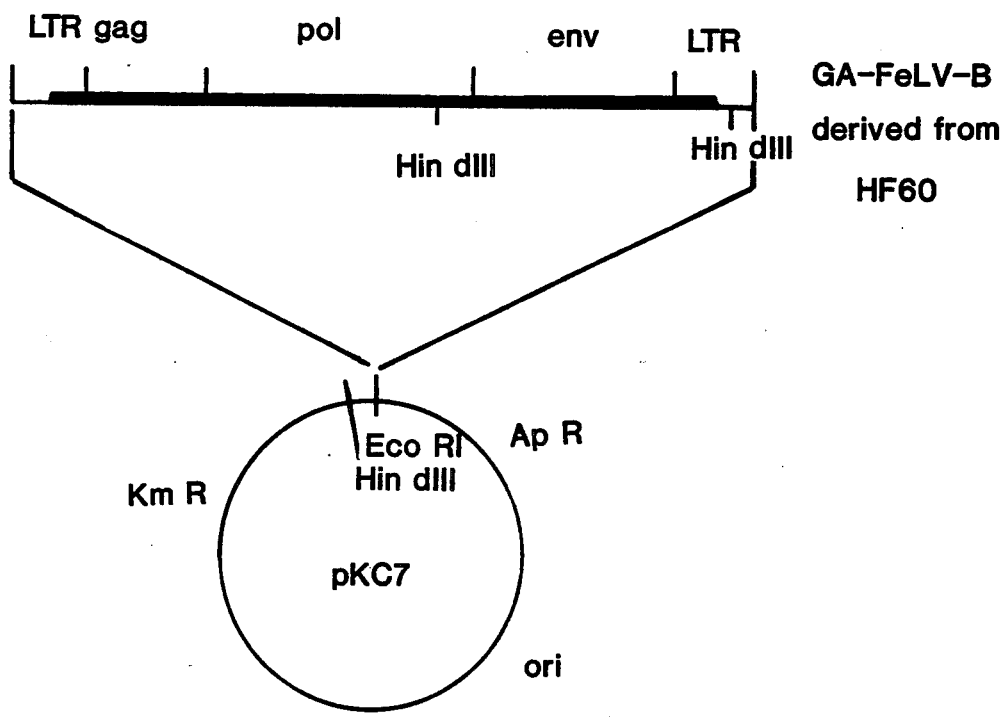
FIG. 1 is a diagram of the plasmid pKHR1 which is the source of the FeLV-B env gene used in the examples.

The microbially produced polypeptides of the invention are distinct from the naturally occurring FeLV envelope proteins in several respects. Although a substantial portion or all of the polypeptides will be homologous to the sequence of a naturally occurring FeLV gp70 protein, in most instances it will comprise only a fraction of the amino acid sequence of the natural gp70 protein. The polypeptides may also include a portion of the p15E protein. Also, since the homologous sequence is produced by microorganisms, it will not be processed (i.e., glycosylated) as natural gp70. Embodiments that are fusion proteins, such as the trp LE'-gp70 fusion proteins, include amino acid sequences that are foreign to natural gp70. The secondary and tertiary structures of such polypeptides may be different from native gp70 because of the lack of glycosylation or the presence of the foreign amino acid sequences. These differences may be reflected in immunological differences.

A preferred group of fusion polypeptides are polypeptides that include a segment of amino acids that is homologous to all or a substantial portion of at least one of the hydrophilic domains of the gp70 protein that occur between about amino acids 210 and 250 and at the gp70-p15E junction, i.e., at between about amino acids 415 and 450 of the gp85 protein, with counting beginning at the presumed start of the gp85 molecule.

A particularly preferred group of polypeptides are those that include one or more iterations of one of the following amino acid sequences (amino acid numbering begins with the presumed start of the gp85 molecule of FeLV-B.)

(a) met gly pro asn leu val leu pro asp gln lys pro pro ser (this sequence occurs at amino acids 213–226 of the gp70 protein of GA FeLV-B);

(b) asp gln lys pro pro ser arg gln ser gln ile glu (this sequence occurs at amino acids 221–232 of the gp70 protein of GA FeLV-B);

(c) pro glu tyr val tyr thr his phe asp lys thr val arg leu (this sequence occurs at amino acids 417–430 of the gp70 protein of ST FeLV-B); and (d) asp lys thr val arg leu arg arg glu pro ile ser leu (this sequence occurs at amino acids 425–437 of the gp85 protein of ST FeLV-B, i.e., the last eight amino acids of the gp70 protein and the first five amino acids of the p15E protein).

As an alternative to the preferred microbially produced fusion polypeptides, the above described segments or sequences (one or more iterations) may be synthesized and coupled to an appropriate protein carrier to produce an effective FeLV immunogen. Cysteines may be added to the segment or sequence to provide coupling sites. Lerner, et al, *PNAS* (1981) 78:3403–3407, describe procedures for coupling small polypeptides to carrier proteins to produce immunogens. Other coupling procedures are described by Church, W. R., et al, *PNAS (USA)* (1983) 80:255, O'Sullivan, M. J. and Marks, V. *Methods in Enzymology* (1981) 73:147–166, and Erlanger, B. F. *Methods in Enzymology* (1980) 70:85–104. Examples of carrier proteins that may be used are keyhole limpet hemocyanin, ovalbumin, porcine thyroglobulin, and bovine serum albumin. Coupling agents for preparing conjugates of the polypeptide and carrier protein include conventional crosslinking agents that are used to couple proteins such as aldehydes (e.g., glutaraldehyde), bisdiazotized benzadine, carbodiimides, succinimides, and imidates.

The invention is herein specifically exemplified with reference to FeLV strains GA and ST (the nucleotide and deduced amino acid sequences of the env genes of these strains are reported by applicant in *J Virol* (1984) 49:630), expression of fusion proteins of trpLE' and FeLV-GA gp70 sequences by *E. coli* transformants, and synthesis of conjugates of antigenic polypeptides homologous to gp70 or gp70-p15E junction sequences and carrier proteins. It will be appreciated, however, that the invention is intended to encompass polypeptides that include sequences that are homologous to gp70 or gp70-p15E sequences of other FeLV strains and subgroups, fusion proteins in which the gp70 sequence is fused to a polypeptide derived from expression of DNA other than the trpLE' sequence, and expression of the polypeptides by transformable microorganisms other than *E. coli*, such as other bacteria and yeasts or viruses, using vectors that can replicate and express heterologous gene sequences in these organisms. Accordingly, the following examples are offered by way of illustration and are not intended to limit the invention in any manner. Abbreviations used in the examples are: DTT, dithiothreitol; ATP, adenosine triphosphate; dTTP, deoxythymidine triphosphate; SDS, sodium dodecyl sulfate; SDS-PAGE, sodium sulfate- polyacrylamide gel electrophoresis; EDTA, ethylenediamine tetraacetic acid; Ac, acetate; BSA, bovine serum albumin; ELISA, enzyme linked immunosorbent assay; DEAE, diethylaminoethyl; ABTS, 2,2'-azino-di-(3-ethylbenzthiazoline sulfonic acid); HF, hydrofluoric acid.

EXAMPLES

General Procedures

All enzymes involved in the manipulation of nucleic acids were obtained from either New England Biolabs or Bethesda Research Labs or were prepared following the manufacturer's recommended procedures. The conditions used for digestion and ligation of DNA, isolation of DNA fragments following gel electrophoresis, as well as transformation of bacterial hosts and selection, are standard procedures well known to those skilled in the art of recombinant DNA. These, and other molecular cloning techniques utilized in practicing the present invention can be found in Maniatis et al, "Molecular Cloning: A Laboratory Manual," Cold Spring Harbor Laboratory (1982).

Digestions of DNA with restriction endonucleases are, unless otherwise stated, to completion and require 1-5 units enzyme/µg DNA for 30-60 min at 37° C. Some digestions are purposefully partial, in that fewer than all sites on each molecule are digested. These are generally done at 0.05-0.5 units enzyme/µg DNA for 10-60 min at 37° C.

Ligations utilizing T4 DNA ligase are performed in 66 mM Tris-HCl, pH 7.6, 6.6 mM $MgCl_2$, 10 mM DTT containing either 0.1 mM ATP and 0.01-0.05 Weiss units ligase/20 µl reaction, for ligation of sticky ends, or 1.0 mM ATP and 1.0-5.0 Weiss units ligase/20 l reaction, for ligation of blunt ends. Reactions are performed at 14° C. for 6-12 hr. Intermolecular reactions require 20-150 µg/ml vector DNA for sticky-end ligation, and 100-200 µg/ml vector DNA for blunt-end ligation. A 1-20-fold excess is maintained in insert DNA over vector DNA. Intramolecular reactions require 10-20 µg/ml vector DNA.

Molecular Cloning and Characterization of GA-FeLV-B

The molecularly cloned GA-FeLV-B provirus was obtained in the form of recombinant DNA molecule in phage lambda as described by Mullins, et al, *J Virol* (1981) 38:688. To summarize, human genomic DNA from cells infected with GA-FeLV-B was digested with EcoRI and molecularly cloned in lambda phage Charon 4A. One such molecularly cloned provirus (lambda HF60) was additionally shown, by the authors, to be infectious when introduced into dog D-170 cells by transfection (Mullins, et al, ibid). The EcoRI fragment of lambda HF60 containing the entire proviral sequence, and flanking human sequence into which the virus has integrated, was subsequently molecularly cloned into the unique EcoRI site of the bacterial plasmid pKC7 (Rao and Rogers, *Gene* (1979) 7:79) and the resulting plasmid, designated pKHR1 is shown in FIG. 1. The orientation of the molecularly cloned provirus was determined relative to the viral RNA genome as described by Mullins, et al, *Nucl Acids Res* (1980) 8:3287.

Figure 2:
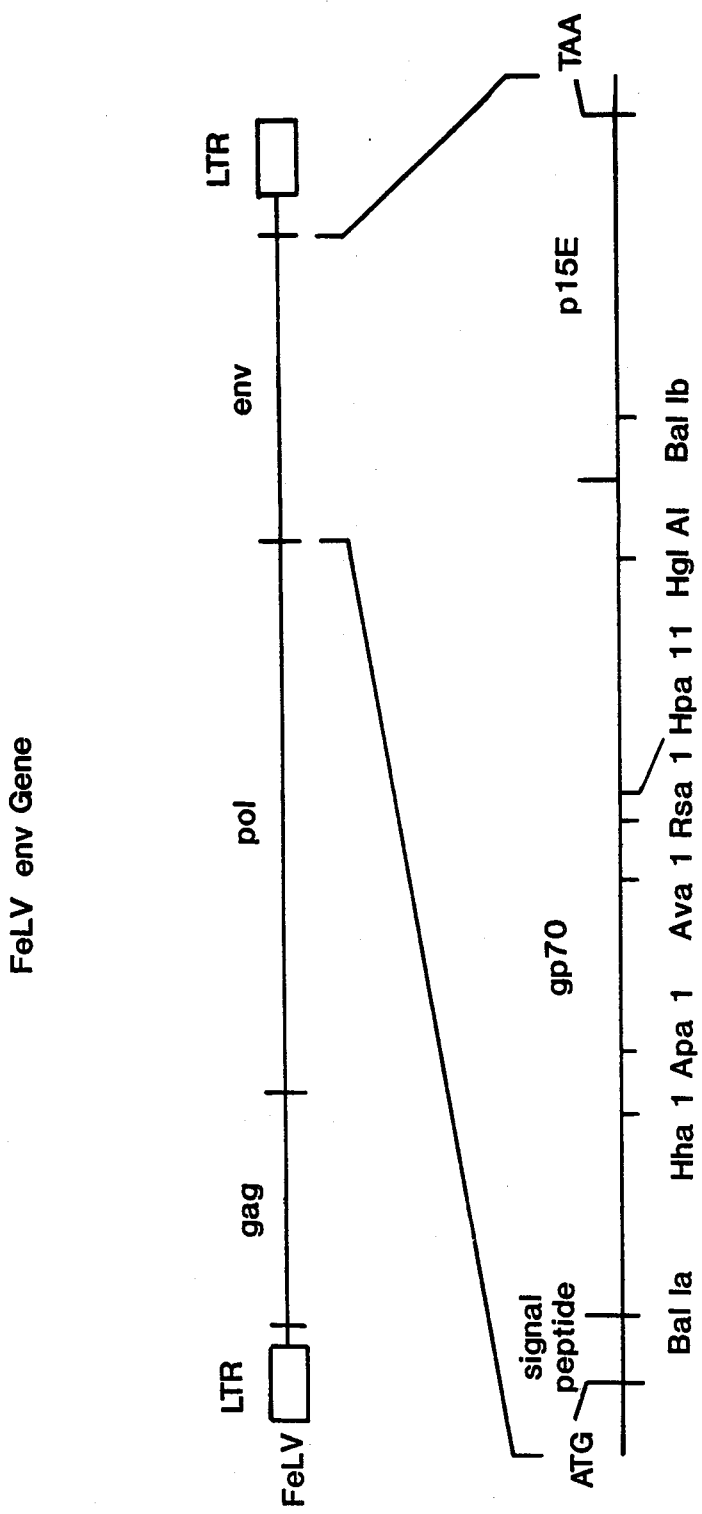
FIG. 2 is a diagram of the FeLV genome including an exploded view of the env gene showing the restriction sites used in making the expression plasmid described in the examples.

FIG. 2 depicts the env gene of FeLV and the locations of the sequences that encode the gp70 and p15E proteins. The env gene encodes a gp85 precursor protein which is transported to the cell membrane of infected cells, and which is cleaved, on virus budding, to the mature viral envelope proteins gp70 and p15E. The gp70 protein is involved in the specific binding of virus to cell receptors, to establish infection, and is known to contain the major antigenic determinants involved in the production of a virus-neutralizing antibody response to infection.

Figures 1, 5:
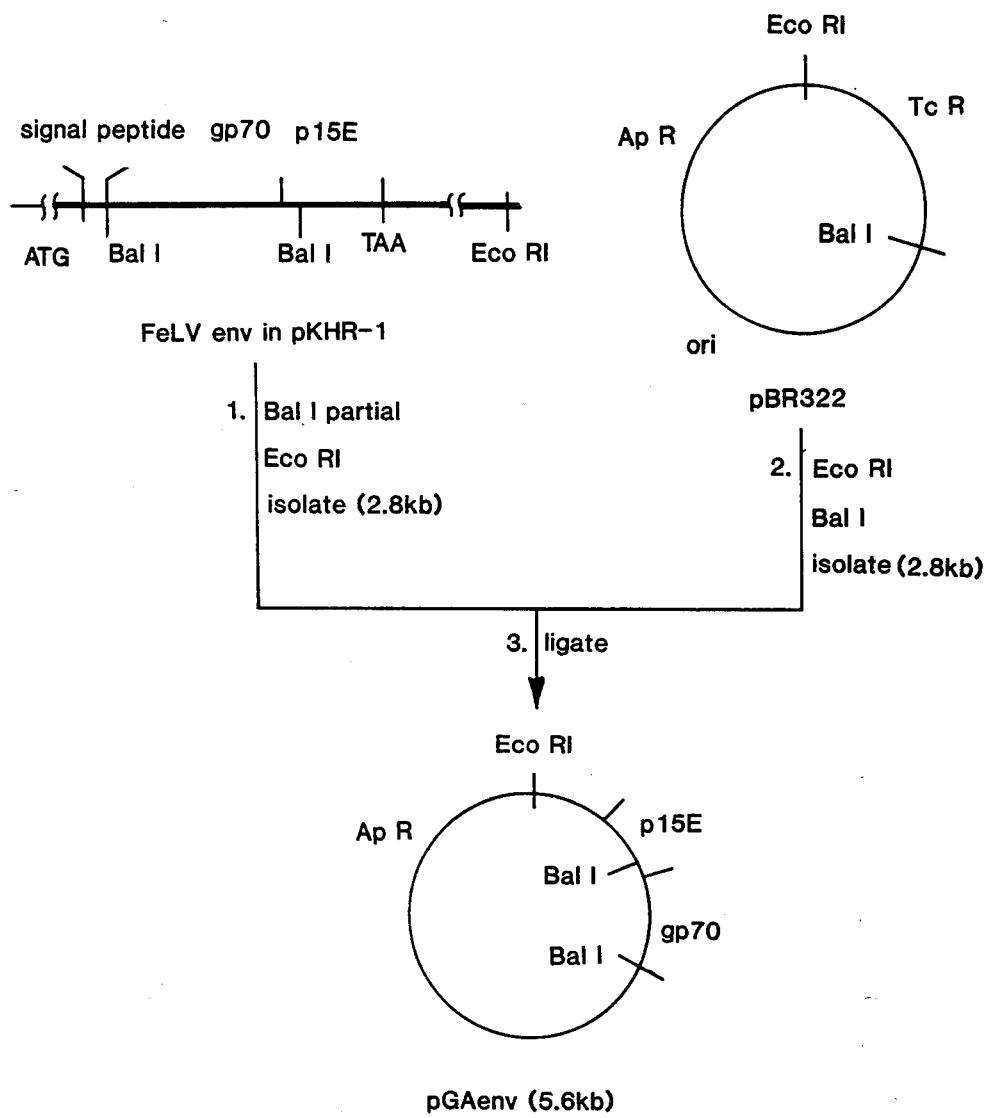
FIG. 5 is a flow chart of the procedure for making the intermediate plasmid ptGA.
Figures 2, 5:
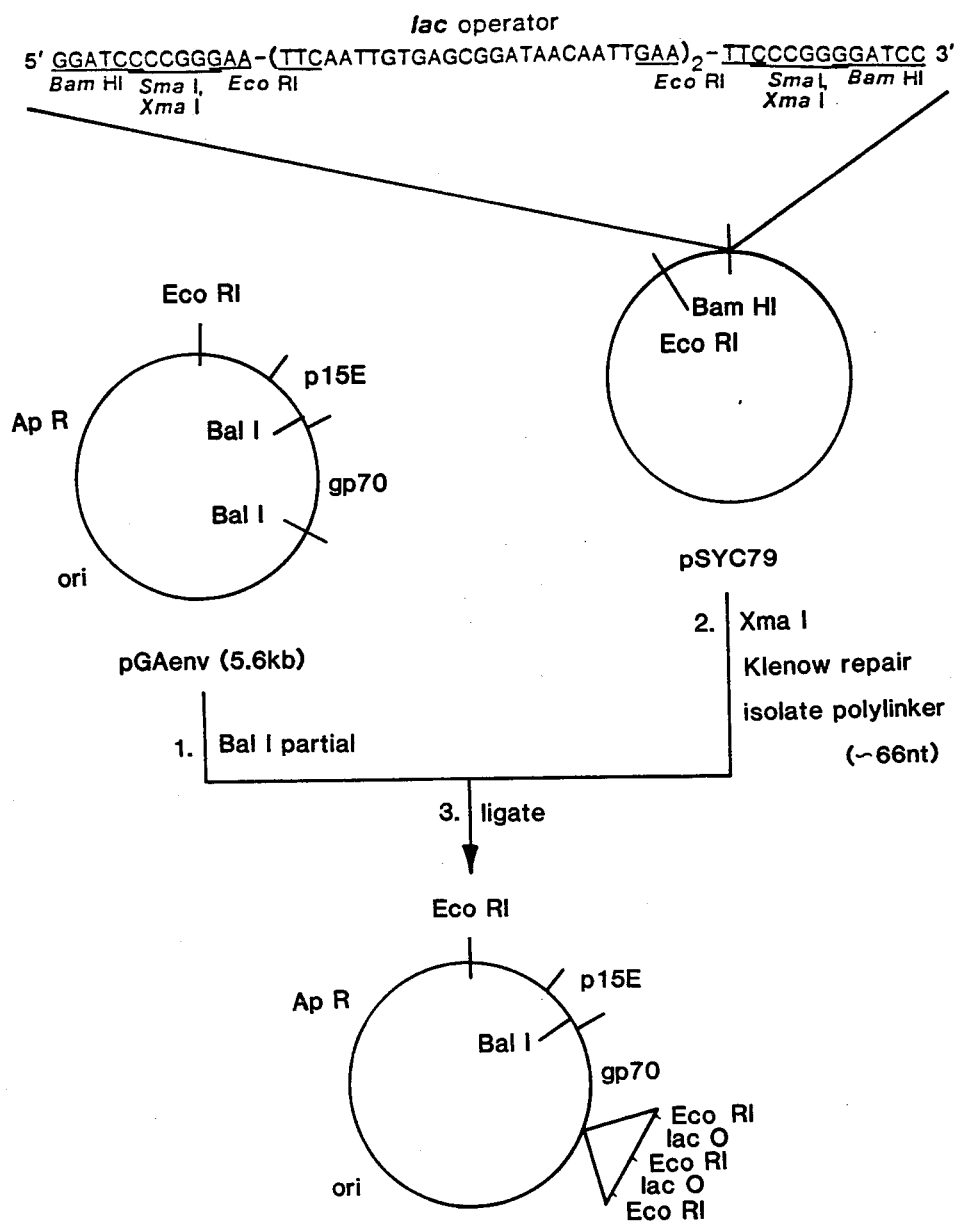
Figures 3, 5:
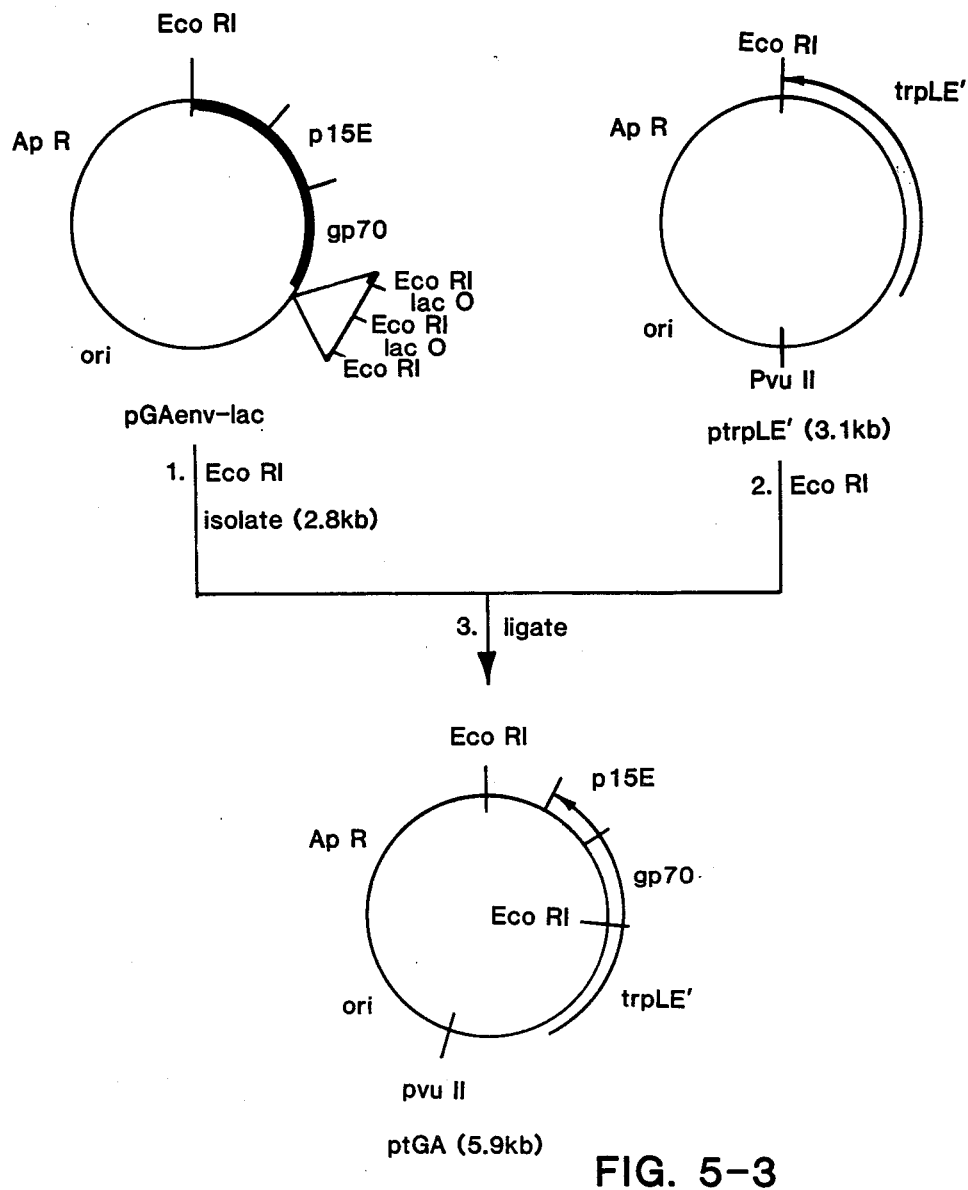
FIG. 3 is the nucleotide sequence of the coding strand of the env gene of the Gardner-Arnstein (GA) strain of FeLV, and the amino acid sequence deduced therefrom.

In order to locate the FeLV env gene, the nucleotide sequence of the 3' portion of the molecularly cloned GA-FeLV-B virus was determined. Standard DNA sequencing methods and strategies were employed (see Maxam and Gilbert, *Meth Enz* (1980) 65:499; Sanger, et al, *PNAS* (1977) 74:5463; Messing, et al, *Nucl Acids Res* (1981) 309). The nucleotide sequence of the GA-FeLV-B env gene and LTR regions, as well as the deduced amino acid sequence of the env gene product, is shown in FIG. 3. Protein sequence homology to known murine leukemia virus p70 and p15E allowed correlation of the respective FeLV proteins with the nucleotide sequence obtained. The sequences are identical to those determined by Elder, J. H. and Mullins, J. I., *J Virology* (1983) 46;871–880.

Construction of ptGA Intermediate

Bacterial plasmids directing the expression of FeLV env antigens contain several elements involved in the expression of a fusion protein including FeLV antigens. With reference to FIG. 4, regions I and II contain, respectively, sequences of the *E. coli* tryptophan promoter/operator/ ribosome binding site and sequences encoding the *E. coli* trp LE' protein (derived from *E. coli* trp Δ LE 1413, Miozzari, et al, *J Bact* (1978) 133:1457 modified so as to introduce an EcoRI site at the C-terminus of the protein-coding region). This trpLE' expresson system has been previously described by Kleid, et al (*Science* (1981) 214:1125 and European patent application no. 81301227.5). The nucleotide sequence of trpLE' is presented in FIG. 7. Region IV contains DNA sequences encoding the various regions of the FeLV env protein. Region III is derived from a synthetic oligonucleotide linker which, if necessary, is used to fuse the trpLE' and FeLV sequences so as to maintain the translational reading frame throughout the entire fused protein.

The bacterial plasmid constructs described here, ptGAΔAvaI, ptGAΔApaI, and pt9:3-19, encode such fusion proteins containing various regions of FeLV gp70. These plasmids were constructed through an intermediate plasmid ptGA containing sequences of the entire FeLV gp85 precursor protein fused to trpLE' as diagrammed in FIG. 5. This strategy takes advantage of a BalI restriction site found at the signal peptide/gp70 junction of the FeLV env gene. The plasmid pKHR1 was partially digested with BalI (0.1–1.0 units/µg DNA, 10–60 min, 37° C.) and then digested to completion with EcoRI (1–5 units/µg DNA, 30–60 min, 37° C.). The desired 2.8 kb fragment, containing sequences from the BalI site at the signal peptide/gp70 junction 3'-ward through gp85 sequences, and terminating at the EcoRI site in human sequence flanking the 3' end of the provirus, was isolated by electrophoresis in agarose gels. This fragment was molecularly cloned into the 2.9 kb BalI-EcoRI fragment of the vector pBR322 containing the ampicillin resistance gene. The vector fragment had been isolated by electrophoresis in agarose gels following complete digestin with BalI and EcoRI (BalI: 1-5 units/μg DNA, 30-60 min, 37° C.; EcoRI: as above). The ligation mixture containing the above pBR322 and FeLV gp85 fragments (T4 DNA ligase 1-20-fold excess FeLV fragment over vector fragment, 10-100 μg/ml vector fragment, 66 mM Tris-HCl pH 7.6, 6.6 mM MgCl$_2$, 10 mM DTT, 0.1 mM ATP, 0.01-0.05 Weiss units/20 μl reaction, 14° C. for 4-12 hr for first step ligation of sticky end EcoRI site; dilute to 10-20 μg/ml vector in above buffer containing 1 mM ATP and 1.0-5.0 Weiss units ligase/20 μl reaction and incubate 14° C. for 12 hr for second step, intramolecular blunt-end ligation of BalI ends) was then used to transform E. coli K12 strain MM294 to ampicillin resistance. Derived plasmids were tested for regeneration of EcoRI and BalI restriction sites. One such plasmid is designated pGAenv (FIG. 5, part 1).

In order to allow molecular cloning of the entire gp85 sequences in the proper reading frame at the EcoI site of the trpLE' expression vector, a synthetic oligonucleotide adapter was used. The nucleotide sequence of the synthetic oligo-nucleotide in the plasmid pSYC 79 is shown in FIG. 5, part 2. Polylinkers, containing BamHI, SmaI/XmaI, EcoRI sites flank two copies of a synthetic E. coli lac gene operator sequence. Plasmids containing the adaptor result in the induction of the bacterial host lac operon, and consequently colonies of these cells show a blue phenotype on X-gal plates. The use of this adaptor in the construction of the ptGA plasmid is shown in FIG. 5, part 2. The plasmid pSYC 79 was digested with XmaI, to cleave the polylinker, and the site was then filled in with Pol I (Klenow fragment) (XmaI: 1-5 units/μg, 30-60 min, 37° C.; Klenow enzyme: repair reaction performed as described in Maniatis, et al, supra, p. 394). The resulting small, blunt-ended adaptor fragment was purified by polyacrylamide gel electrophoresis. The plasmid pGAenv was partially digested with BalI (above) and ligated to the purified adaptor fragment (T4 DNA ligase: intermolecular blunt-end ligation performed as above (intramolecular) but at 200 μg/ml vector and 20-100-fold excess adaptor). This material was used to transform E. coli K12 MM294 to ampicillin resistance and blue phenotype on X-gal plates. Resulting plasmids were analyzed with EcoRI, to demonstrate insertion at the desired BalI site, and with HaeIII, to confirm proper fusion at the adaptor/BalI site junction. The latter was confirmed by DNA sequencing of the junction. One such plasmid is designated pGAenv-lac (FIG. 5, part 2).

Figure 6:
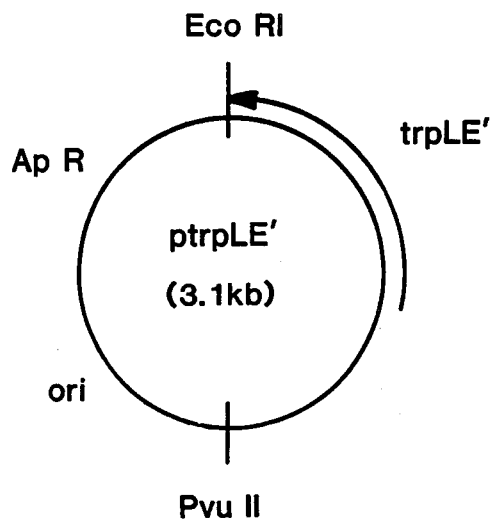
FIG. 6 is a diagram of the plasmid ptrpLE'.
Figure 8:
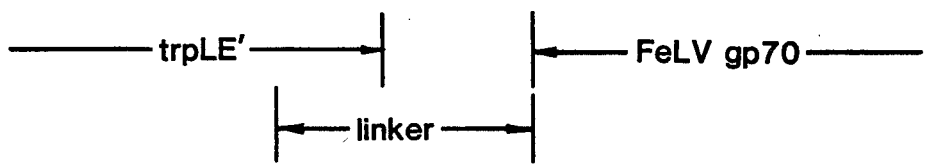
FIG. 8 is the nucleotide sequence and deduced amino acid sequence at the trpLE'/gp70 junction in the plasmid ptGA.

The resulting 2.8 kb EcoRI fragment of pGAenvlac containing adapted FeLV gp85 sequences was isolated by electrophoresis following digestion with EcoRI (as above), and was ligated (T4 DNA ligase sticky-end ligation as above) to ptrpLE' which had also been digested with EcoRI (as above). The plasmid ptrpLE' contains sequences of the E. coli trp Δ LE 1413 operon from the PvuII site 285 bp upstream of the trpLE' gene ATG codon to the EcoRI site generated at the C-terminus of the LE' gene (the trp Δ LE 1413 sequence is described in European patent application no. 81301227.5). This PvuII-EcoRI fragment had been molecularly cloned into the PvuII-EcoRI fragment of pBR322. The resulting plasmid, shown in FIG. 6, confers ampicillin resistance and encodes the trpLE' protein fragment. FIG. 7 shows the nucleotide sequence of the LE' gene and the deduced amino acid sequence The ligation mixture containing the ptrpLE' vector and the 2.8 kb FeLV gp85 fragment was used to transform E. coli K12 MM294 to ampicillin resistance and white phenotype on X-gal plates. Resulting plasmids were analyzed witn EcoRI, to confirm regeneration of sites, and with HindIII plus PvuII, to determine the orientation of the inserted EcoRI fragment. One plasmid, containing an insert in the proper orientation, is designated ptGA. This plasmid, shown in FIG. 5, part 3, contains the FeLV gp85 sequences fused, in the proper reading frame, to the trpLE' expression vector. The nucleotide sequence and deduced amino acid sequence at the trpLE'/gp70 junction in ptGA are shown in FIG. 8. This plasmid was used as an intermediate in subsequent constructions of the plasmids ptGAΔΔAvaI, ptGAΔΔApa, and pt9:3-19.

Construction of ptGAΔΔAvaI

Figures 1, 9:
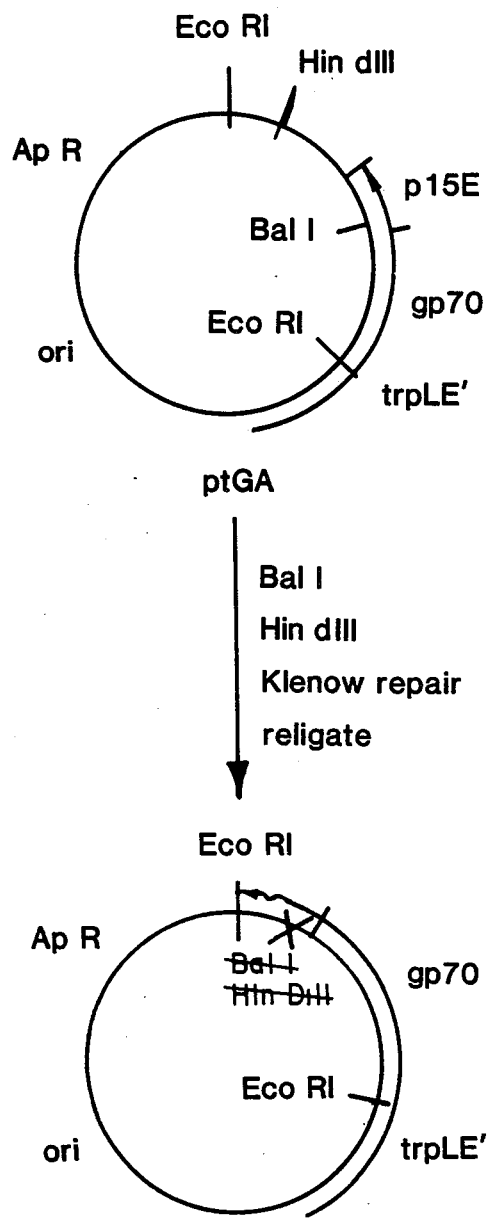
FIG. 9 is a flow chart of the procedure for making the plasmid ptGAΔAvaI.
Figure 9:
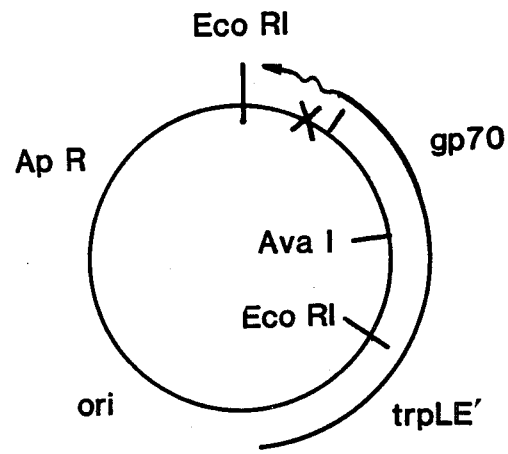
Figure 2:
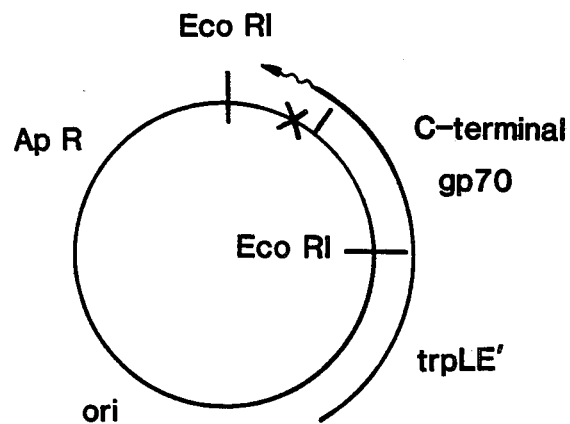

The ptGAΔΔAvaI plasmid encodes a trpLE' fusion protein containing approx. 240 amino acids derived from the C-terminal half of FeLV gp70 and the N-terminal region of p15E. This plasmid was derived from ptGA as outlined in FIG. 9, through an intermediate construction ptGA BalI-HindIII in which sequences of ptGA between the unique BalI site, in sequences encoding p15E, and the unique HindIII site, in sequences flanking the 3'-end of the integrated FeLV provirus in pKHR1, were deleted. ptGA BalI-HindIII was constructed as follows. ptGA was digested with BalI and HindIII and the HindIII sites repaired with Klenow fragment, as described above. This material was then ligated (T4 ligase: intramolecular blunt-end conditions as above) and used to transform E. coli to ampicillin resistance. Plasmids of resultant colonies were screened to ensure deletion of 1.0 kb from the 2.8 kb EcoRI fragment containing the FeLV sequences. Translation terminates at an adventitious termination codon in sequences distal to the HindIII site. This plasmid, ptGA BalI-HindIII, was then used to generate ptGAΔΔAvaI.

The plasmid was digested to completion with AvaI (AvaI: 1-5 units/μg DNA, 30-60 min, 37° C.) and partially digested with EcoRI (EcoRI: 0.05-0.2 units/μg DNA, 10-30 min, 37° C.). The ends were repaired with Klenow fragment and the approximately 4 kb AvaI-partial EcoRI fragment isolated by gel electrophoresis. This was then allowed to recircularize (T4 DNA ligase: intramolecular blunt-end conditions as above) and used to transform E. coli to ampicillin resistance. Plasmids of derived colonies were screened for regeneration of the EcoRI site at the ligation site at the trpLE'-FeLV sequence junction. The translational reading frame is maintained across this junction. This plasmid is designated ptGAΔΔAvaI.

Construction of ptGAΔΔApaI

Figures 1, 10:
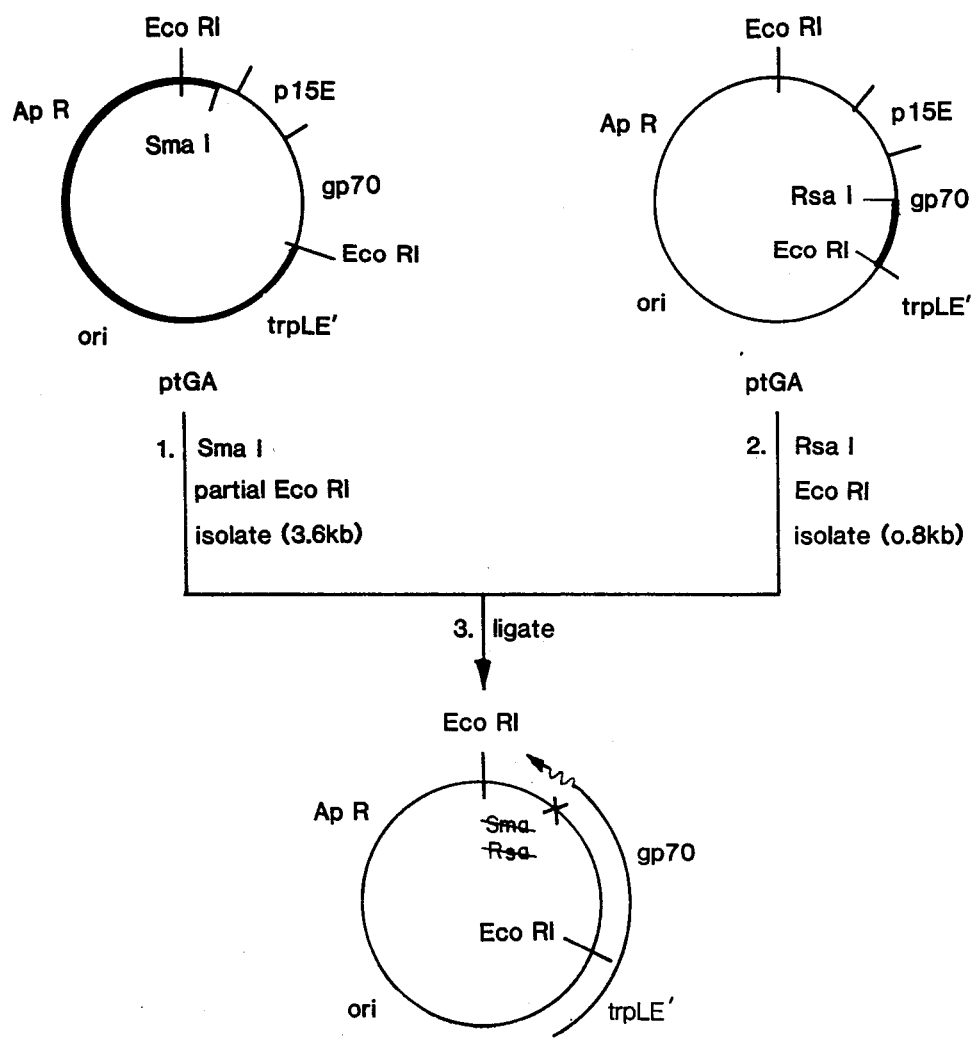
FIG. 10 is a flow chart of the procedure for making the plasmid ptGAΔApaI.
Figures 2, 10:
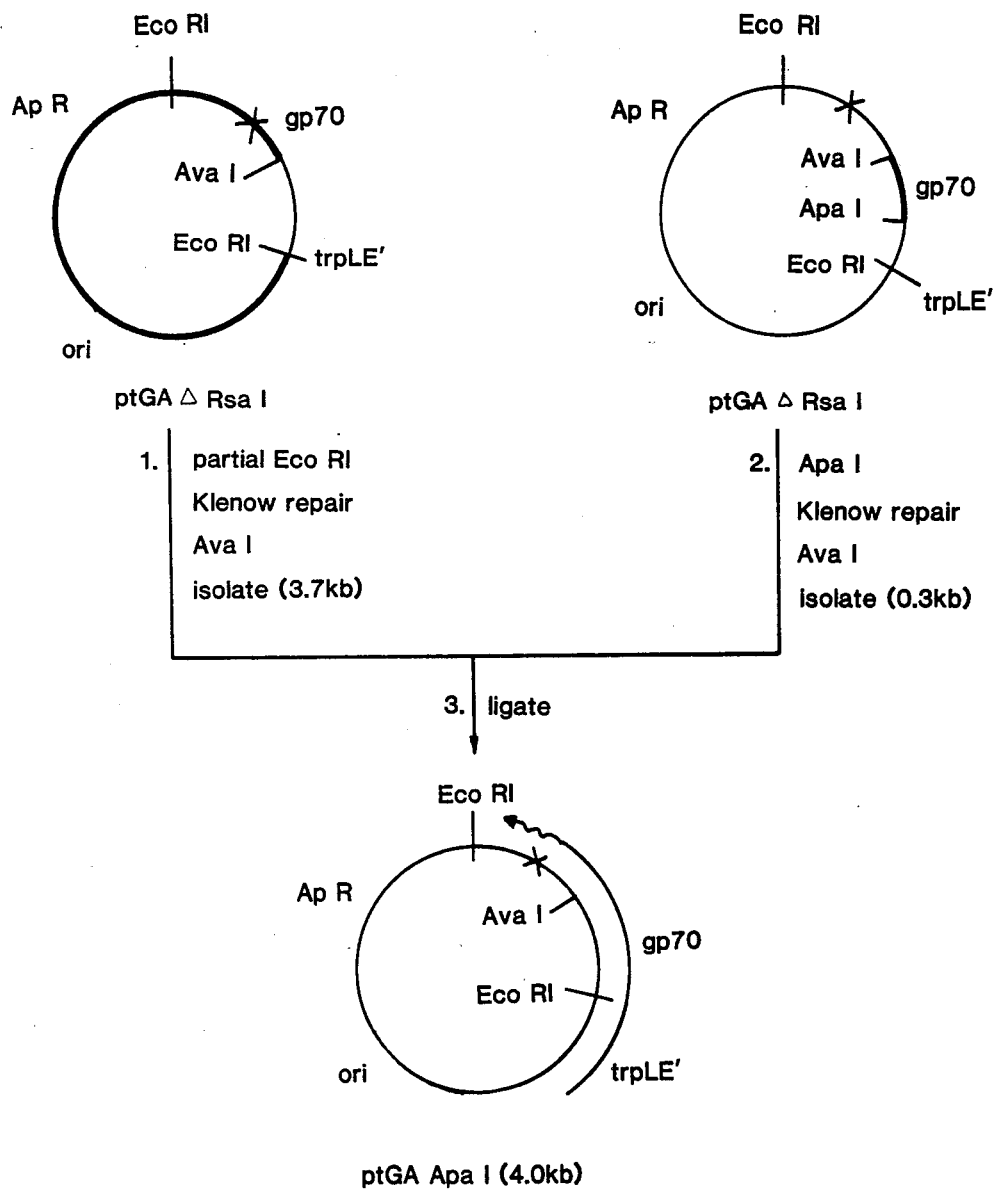

The plasmid ptGAΔΔApaI encodes a trpLE' fusion protein containing approx 120 amino acids of gp70 derived from amino acids 176-293 of the env gene product. This plasmid was derived from ptGA as diagrammed in FIG. 10 through an intermediate construction ptGA RsaI in which gp70 encoding sequences distal to the RsaI site at amino acid 293-294 have been deleted. ptGA RsaI was constructed as follows (FIG. 10, part 1). ptGA was digested to completion with SmaI (SmaI: 1-5 units/μg DNA, 30-60 min, 37° C.) and then partially digested with EcoRI (EcoRI: 0.05-0.2 units/μg DNA, 10-30 min, 37° C.) and the approximately 3.4 kb vector fragment isolated. The plasmid ptGA was also digested to completion with EcoRI (EcoRI: 1-5 units/μg DNA, 30-60 min, 37° C.) and with RsaI (RsaI: 1-5 units/μg DNA, 30-60 min, 37° C.) and the 780 bp EcoRI-RsaI fragment containing sequences encoding the amino terminal half of gp70 isolated. This fragment was ligated to the vector (T4 ligase: two step process; intermolecular sticky end, plus intramolecular blunt end) and the mixture was used to transform E. coli to ampicillin resistance. Resulting plasmids were screened, using EcoRI, and the desired plasmid is indicated ptGAΔRsaI.

The plasmid ptGAΔΔApaI is derived from ptGAΔRsaI by deletion of sequences encoding the amino terminus of gp70 to the ApaI site at sequences encoding amino acid 174-175 of gp70. ptGAΔΔApaI was constructed as follows (FIG. 10, part 2): the plasmid ptGA RsaI was partially digested with EcoRI (EcoRI: 0.05-0.2 units/μg DNA, 10-30 min, 37° C.) and the sticky ends repaired with DNA polymerase I (Klenow fragment) in the presence of nucleotide triphosphates, as described above). This material was then digested to completion with AvaI (AvaI: 1-5 units/μg DNA, 30-60 min, 37° C.) to isolate the 3.7 kb vector fragments. This same plasmid, ptGAΔRsaI, was also digested to completion with ApaI (ApaI: 1-5 units/μg DNA, 30-60 min, 37° C.) and the sticky ends repaired as above. The isolated 280 bp ApaI-AvaI fragment was then ligated to the vector, in a two step process as above, and the mixture used to transform E. coli to ampicillin resistance. Transformants were screened for regeneration of the EcoRI site at the EcoRI/repair-ApaI/repair junction, as well as for expression of antigen. Proper ligation of the repaired EcoRI and the ApaI sites results in the in-frame fusion of trpLE' and FeLV sequences. The desired plasmid is designated ptGAΔΔApaI.

Construction of pt9:3-19

The plasmid pt9:3-19 encodes a trpLE' fusion protein containing 14 amino acids of gp70 that comprise an antigenic domain of the FeLV env antigen. The location of this domain was determined by mapping the virus with a virus neutralizing monoclonal antibody as follows: Hybridomas secreting antibodies directed against the complex of gp70 and p15E proteins of FL-74 FeLV (prepared as described by Schneider, J., et al, *J Virology* (1980) 33:597-605) were derived from spleen cells from mice immunized with gp70/p15E complex as described by Lutz, H., et al, *J Immun Methods* (1983) 56:209-220. Samples of these monoclonal antibodies were obtained from Dr. Niels Petersen, Department of Medicine, UC Davis School of Veterinary Medicine. Several monoclonal antibodies were examined for the ability to neutralize FeLV in a focusforming assay using CCC cl.81 (S+,L-) cells. One gp70 monoclonal antibody, designated cl.25, was able to neutralize all viruses tested, of all FeLV subgroups, with the exception of the FL-74 FeLV-B. This antibody was used to determine the site on the gp70 molecule involved in virus neutralization by this monoclonal antibody.

Figure 11:
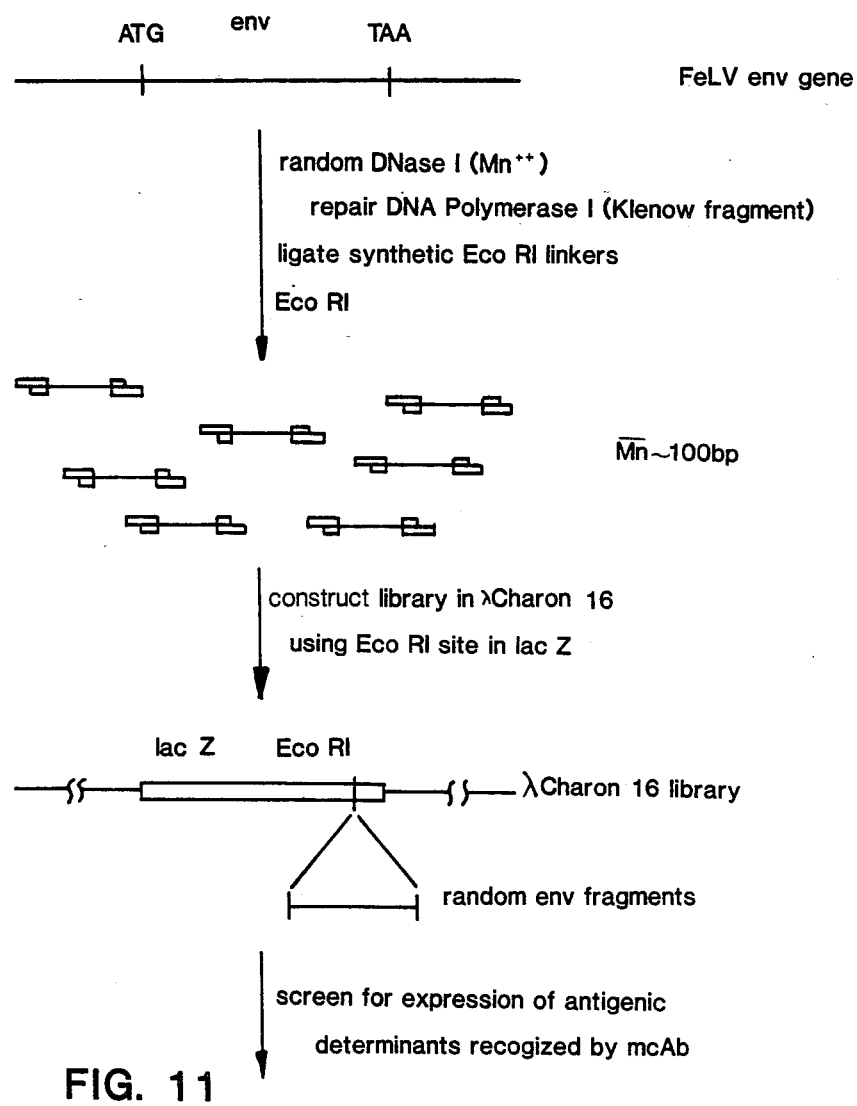
FIG. 11 is a flow chart of the procedure for identifying an antigenic determinant of the gp70 molecule.

The procedure used to locate this site is shown in FIG. 11. pKHR1 was digested with XhoI and EcoRI. The 3.1 kb XhoI-EcoRI fragment of this plasmid, containing the entire 2.0 kb of envelope-encoding sequences, was isolated and digested with DNaseI, in the presence of Mn++, to a mass average molecular weight of approximately 500-700 bp as judged from EtBr-staining of analytic agarose gels. This corresponds to a number average molecular weight of approximately 100 bp, based on analysis of end-labelled fragments. Fragments were made blunt-ended by treatment with DNA polymerase I (Klenow fragment) in the presence of nucleotide triphosphates and ligated to an excess of 32P-labelled synthetic EcoRI linker (5'-$^{32}$P-GGAATTCC). Following digestion with EcoRI, to generate sticky-ends, fragments were fractionated on cellulose (CF-11, Whatman) to remove linker monomers and residual triphosphates. This material was then molecularly cloned into the EcoRI site encoding amino acids 1004-1005 (Glu-Phe) of the β-galactosidase gene in phage Charon 16. The Charon 16 phage DNA had previously been digested with EcoRI, and the 5' ends dephosphorylated using bacterial alkaline phosphatase to maximize insertion frequency. EcoRI-digested phage DNA and EcoRI-adapted fragment DNA were ligated and the ligation mix packaged in vitro as described by Sternberg, N., et al, *Gene* (1977) 1:255-280. Approximately 30,000 independent plaques were derived; roughly 10% contained inserts as judged by in situ plaque hybridization using, as probe, the original XhoI-EcoRI FeLV fragment. Staining patterns of plaques grown on plates containing X-gal were also indicative of insertion frequency; phage containing inserts within the β-galactosidase gene produced either white plaques, or plaques showing a faint blue ring at the plaque margin. Ten percent of this library was amplified and used in immunoscreening.

In order to assess the ability to detect expression in E. coli of a β-galactosidase fusion protein containing the antigenic determinant recognized by cl.25, a recombinant phage, Charon 16:GA, was constructed in which sequences encoding the entire mature FeLV gp85 were fused, in frame, to the EcoRI site of Charon 16. Using a synthetic polylinker, the BalI site at sequences encoding the envelope signal peptide/gp85 junction was adapted to create an EcoRI site as described above (ptGA) and to allow an in-frame fusion with the EcoRI site of β-galactosidase. Uncloned phage from this experiment were screened for expression of the cl.25 determinant. Purification of phage identified by the antibody was followed both by repeated immunoscreening and by staining with X-gal. Purified phage were shown to contain the expected FeLV sequences, in the expected orientation, and were further shown to produce a fusion protein detectable by cl.25 in Western analysis, see below.

Initial immunoscreens of the random DNA fragment library were performed at a plaque density of approximately $10^3$ per 100 mm plate. Using the simplest of assumptions, this corresponds, in this experiment, to an expectation of one immune-reactive plaque per two plates. This expectation was realized in these initial screens; 11 immune-reactive plaques were chosen for purification by repeated immunoscreens. Of the initial 11 plaques chosen for examination, all but one gave consistently reliable signals allowing purification. X-gal staining patterns were again useful in this procedure. Purified phage were homogeneous as judged by immune-reactivity and X-gal staining.

DNA was isolated from immune-reactive phage and the structure of these recombinant phage examined by restriction endonuclease analysis. Phage DNAs were digested with EcoRI, to liberate the insert fragment(s), and DNA polymerase I (Klenow fragment) was used to label the EcoRI ends using dTTP and $^{32}$P-dATP. Polyacrylamide gel analysis showed all immune-reactive isolates to be identical; all contained one unique 50 bp EcoRI fragment. This finding is in keeping with estimates derived from consideration of the complexity of the amplified library used in screening.

Figure 12:
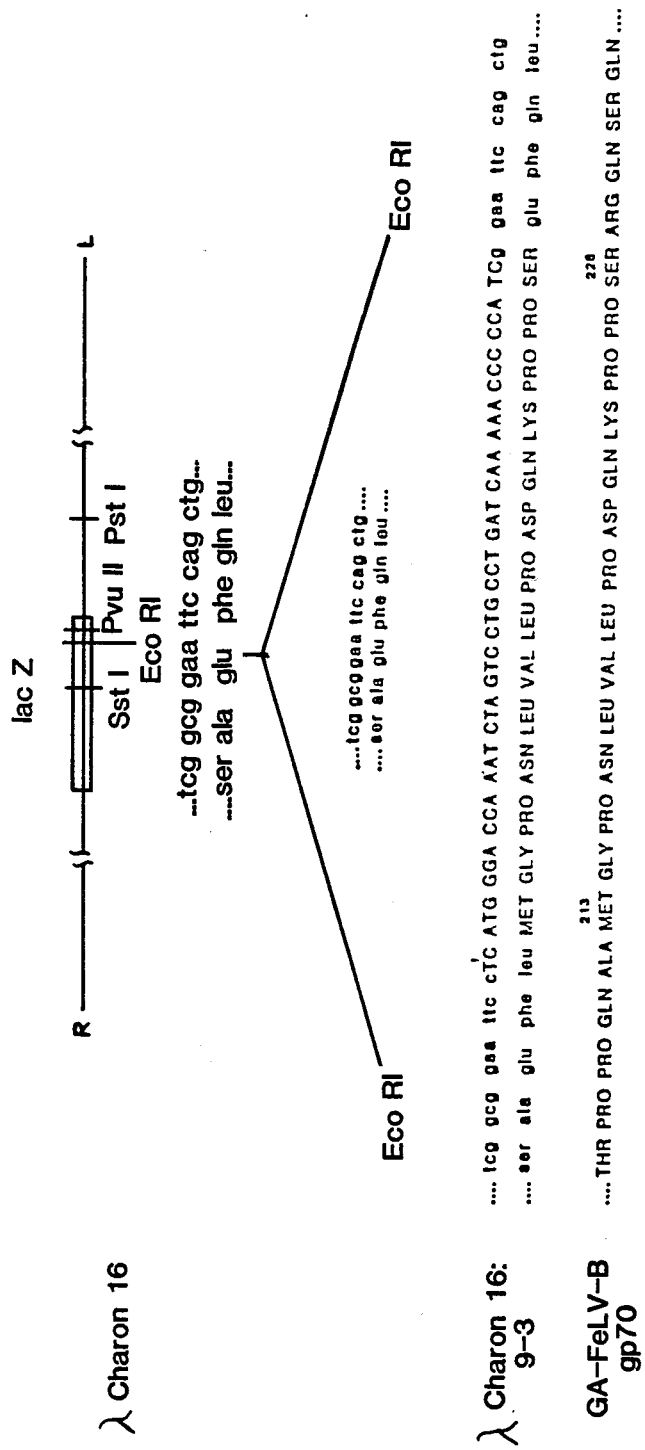
FIG. 12 is the nucleotide sequence and deduced amino acid sequence of the antigenic domain identified by the procedure of FIG. 11.

To expedite DNA sequence analysis of the 50 bp fragment involved in immune-reactivity, a region of the phase DNA containing the EcoRI insertion site of Charon 16:9-3 was subcloned into the plasmid pUC13 (Vieira, J. and Messing, J., unpublished, Bethesda Research Labs catalog (1983). A fragment spanning the region from the unique SstI site encoding amino acids of the β-galactosidase gene (FIG. 12), through the EcoRI site, to a PstI site located beyond the lac operon fragment of Charon 16. DNA sequence analysis was performed using the chemical sequencing procedures of Maxam and Gilbert; sequence was read from the PvuII site directly 3' of the EcoRI cloning site. Sequence analysis demonstrates an insert of 43 bp of the GA-FeLV envelope gene flanked by synthetic EcoRI linker sequences. This represents nucleotides 635–678 of the region of the env gene encoding gp70 and is present so as to give rise to an inframe fusion protein with both upstream, and downstream, β-galactosidase sequences. The sequence of the encoded gp70 fragment (amino acids 213–226 of gp70) is shown in FIG. 12. The capital letters in the sequences denote the FeLV sequences. The dagger symbol in the λ Charon 16:9-3 nucleotide sequence indicates a T→C mutation. The antigenic determinant recognized by cl.25 is contained within this 14 amino acid region.

Figure 13:
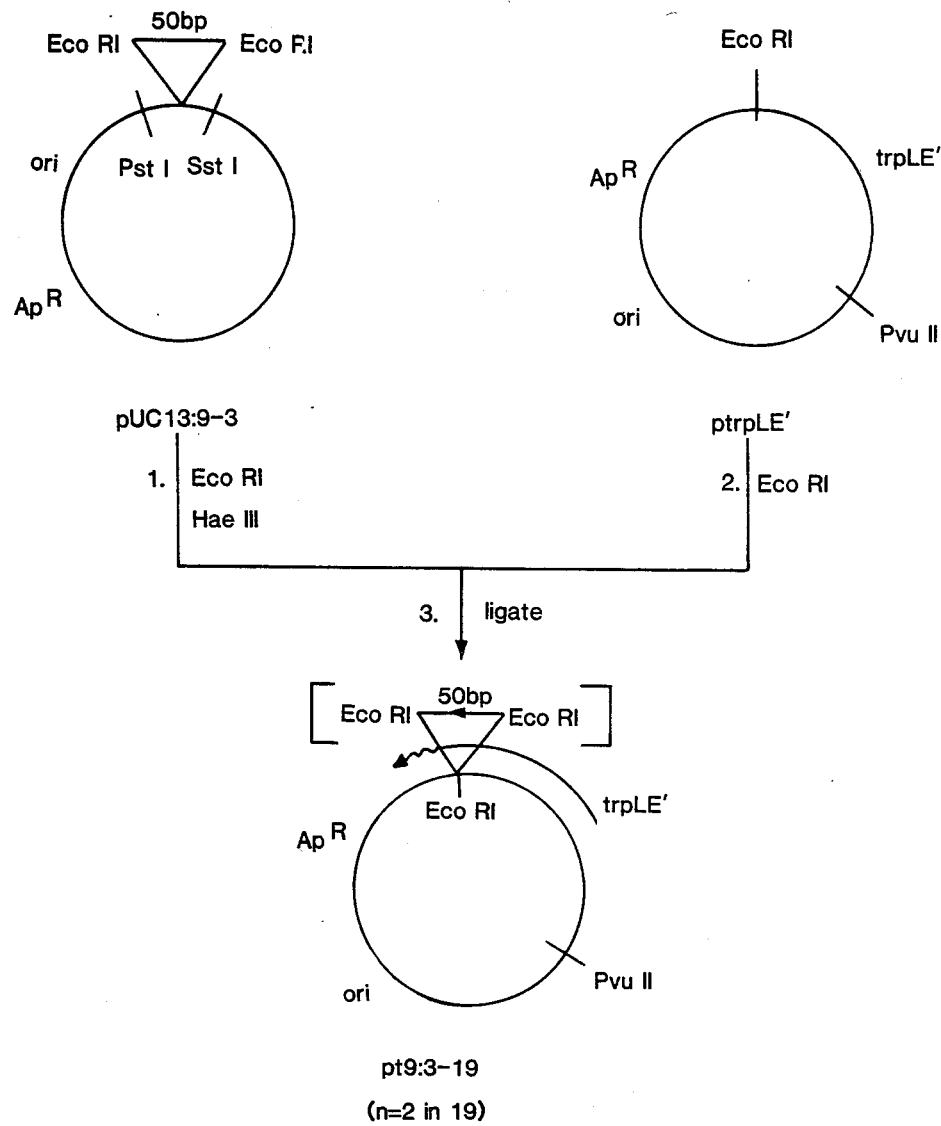
FIG. 13 is a flow chart of the procedure for making the plasmid pt9:3-19.

This 50 bp EcoRI fragment was molecularly cloned into the EcoRI site of ptrpLE' to obtain expression of the antigenic determinant as a fusion protein with trpLE' as shown in FIG. 13. The subcloning plasmid pUC13:9-3 was digested to completion with EcoRI (EcoRI: 1–5 units/µg DNA, 30–60 min, 37° C.), to liberate the EcoRI-fragment, and with HaeIII (HaeIII: 1–5 units/µg DNA, 30–60 min, 37° C.), to inactivate the pUC13 vector. This mixture was then ligated (T4 ligase: intermolecular sticky end) to ptrpLE' which had previously been digested to completion with EcoRI and used to transform *E. coli* to ampicillin resistance. Transformants were screened for expression of the cl.25 determinant by immunologic analysis of expressed proteins (as described below) using cl.25 to detect antigen. Several isolates were found to contain an antigenic fusion protein of a size indicative of one inserted EcoRI fragment; one isolate, pt9:3-19, was found to contain two inserts and to be highly antigenic.

Samples of *E. coli* K12 strain MM294-1 transformed with the plasmids ptGAΔΔAvaI, ptGAΔΔApaI, and pt9:3-19 were deposited at the American Type Culture Collection (ATCC), 12301 Parklawn Drive, Rockville, Md. Their deposit date and accession numbers are listed below.

| Sample | Deposit Date | ATCC Accession No |
|---|---|---|
| ptGAΔΔAvaI | 2 December 1983 | 39528 |
| ptGAΔΔApaI | 2 December 1983 | 39529 |
| pt9:3-19 | 2 December 1983 | 39530 |

These deposits were made under the Budapest Treaty and will be maintained and made available in accordance with the provisions thereof.

Cultivation

*E. coli* containing trpLE' fusion plasmids are typically grown under non-inducing conditions in M9 minimal medium (Maniatis, et al, supra) plus glucose (0.2%), 1 µg/ml B1, Casamino Acids (0.5%, charcoal treated), tryptophan (100 µg/ml) and ampicillin (50 µg/ml). *E. coli* cells are induced to express trpLE' fusion proteins in a variety of ways including (a) washing growing cells into medium above lacking tryptophan, (b) washing growing cells into medium above containing a limiting tryptophan, e.g., 2–5 µg/ml, or (c) allowing culture to deplete tryptophan supplies by growth, e.g., in fermenter. In some cases, cells are found to be partially induced in the presence of tryptophan. Furthermore, these cells often contained a larger proportion of undegraded fusion protein than under induced conditions. Similar results are often obtained in overnight cultures in rich medium.

Detection of trpLE' Fusion Protein

Induction of trpLE'-FeLV fusion protein, by any of the methods above, results in the appearance of highly refractile particles within cells carrying the plasmid. These particles are visible in the microscope, using phase optics (1250x), and are characteristic of the synthesis of LE' fusion proteins.

Characterization of Expressed Protein

Figure 14:
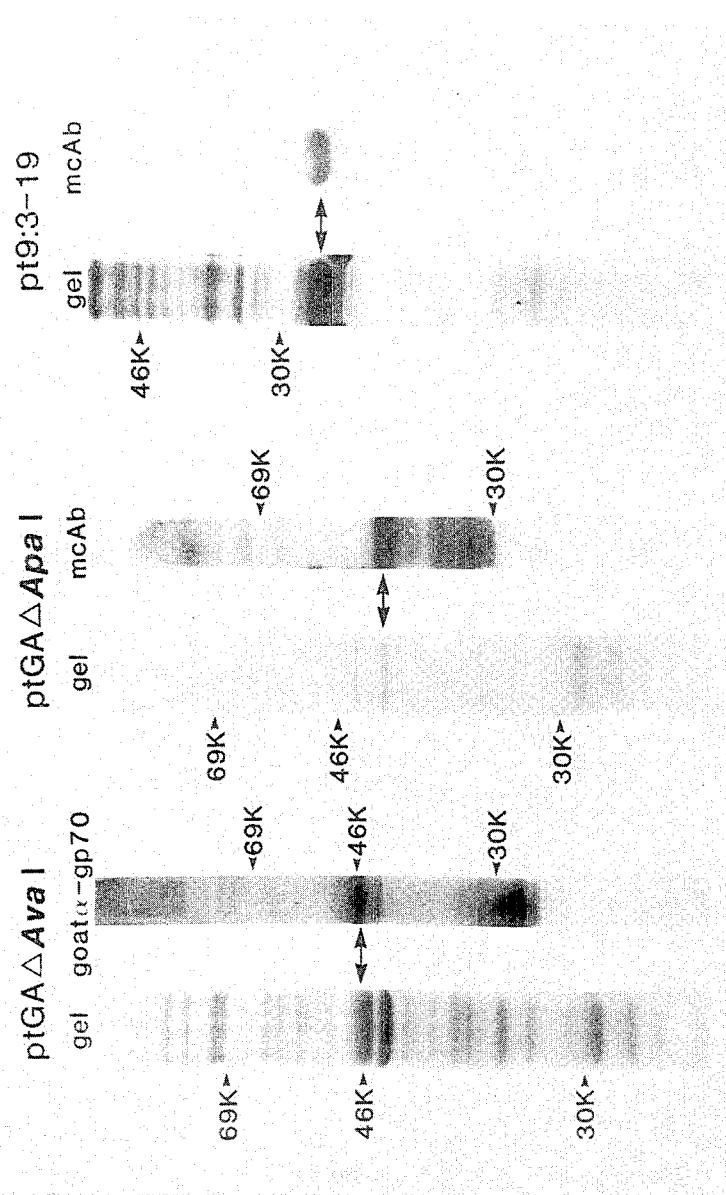
FIG. 14 is an electrophoretogram of the SDS-PAGE analyses of the protein products of ptGAΔAvaI, ptGAΔApaI, and pt9:3-19.

Protein products of cells containing plasmids were analyzed by SDS-PAGE (Laemmli U.K., *Nature* (1970) 227:680). Cells grown under induced, or non-induced conditions, were sonicated and boiled in sample buffer prior to electrophoresis. FIG. 14 shows a gel, stained with Coomassie Blue, of protein products from cells containing the ptGAΔΔAvaI, ptGAΔΔApaI and pt9:3-19 plasmids. The ptGAΔΔAvaI plasmid encodes the expected 46 kd protein; smaller degradation products are observed. The ptGAΔΔApaI plasmid encodes a 36 kd protein; smaller degradation products are observed. The pt9:3-19 plasmid encodes a 25 kd fusion protein.

These protein products were analyzed immunologically by Western analysis, using modifications of a method first described by Towbin, et al, *PNAS* (1979) 76:4350. Proteins are resolved by SDS-PAGE, and the pattern is then transferred electrophoretically to a solid support, e.g., CNBr-activated paper. This paper is then reacted with specific antibodies, e.g., antibodies to FeLV gp70, and protein bands reacting with antibody are visualized, e.g., using $^{125}$I-labelled Staph aureus protein A (Ivarie and Jones, *Anal Biochem* (1979) 97:24). Using either cl.25 or goat anti-FeLV gp70 antibody, it was confirmed that the protein products observed in FIG. 14 contain FeLV gp70 protein sequences.

Purification of FeLV Antigen

Refractile particles from induced cells containing ptGA were purified by centrifugation. Cells were resuspended in buffer containing 50 mM Tris-HCl, pH 8.0, 5 mM EDTA, 150 mM NaCl and 0.2% NP-40 and sonicated. The lysate was subjected to low speed centrifugation; the pellet, containing predominantly particles of FeLV antigen, was washed by several subsequent cycles of resuspension, sonication, and centrifugation. The final product can be resuspended in buffer, or can be solubilized with 1% SDS, in the presence or absence of reducing agent.

Antigen was also prepared from solubilized whole cell lysates. Induced cells are sonicated in buffer containing 50 mM Tris-HCl pH 7, 10 mM EDTA, 50 mM DTT and 2% SDS. Lysates are heated briefly (100° C./5 min) to fully denature the protein, and insoluble debris is removed by centrifugation. This lysate is then fractionated by gel filtration chromatography (Sephacryl S-200 in buffer containing 50 mM NaOAc, pH 5.5, 0.5 mM EDTA, 2 mM DTT and 0.1% SDS) and all fractions 20 kd pooled and concentrated.

Prior to immunization, all SDS containing samples are dialyzed to a final SDS concentration of 0.1%. Once solubilized in higher % SDS, the proteins are soluble in 0.1% SDS.

Approximately 0.1–20 mg protein is compounded with an appropriate adjuvant (complete Freund's, incomplete Freund's, aluminum hydroxide, or a synthetic adjuvant), and used to inoculate cats.

Synthesis of gp70 and gp70-p15E Junction Sequences and Coupling to Carrier Proteins The following polypeptides were synthesized using a SAM II automatic peptide synthesizer (Biosearch, Inc., San Rafael, CA)

Peptide I

H - cys asp lys thr val arg leu arg arg glu pro ile ser leu - OH

Peptide II

H - cys pro glu tyr val tyr thr his phe asp lys thr val arg leu - OH

Peptide III

H - cys met gly pro asn leu val leu pro asp gln lys pro pro ser - OH

Peptide IV

H - asp gln lys pro pro ser arg gln ser gln ile glu cys ser - OH

Conjugates of these polypeptides and bovine serum albumin, keyhole limpet hemocyanin or porcine thyroglobulin were made as follows. Eleven mg of N-maleimido-6-aminocaproyl-2'-nitro-4'-sulfonic acid sodium salt is added to a solution of 22 mg of carrier protein in 6 ml of 0.1 M phosphate, pH 7.5. After 15 min the solution is chromatographed on a Sephadex G-25 column in 0.1 M phosphate, pH 6. Protein-containing fractions are pooled and treated with 18 mg of the polypeptide. The reaction is allowed to proceed overnight, the solution is dialyzed against 6l H20, chromatographed on a Sephadek G-50 column in 0.01 N NH$_4$OH, lyophilized and analysed.

Approximately 0.1–20 mg of each conjugate is compounded with an adjuvant for use in vaccinating test animals.

The above described fusion proteins and peptide-carrier protein conjugates are tested as FeLV vaccines in cats and guinea pigs as follows.

Cat Trials: Immunogenicity and Efficacy

Immunogenicity may be evaluated by determining the presence of anti-gp70 antibodies and FeLV neutralizing antibodies in the serum of cats vaccinated with the polypeptides. Immunoprotection may be evaluated by observing the effects of FeLV on the vaccinated cats. The following procedures are used in these evaluations.

Young FeLV-free cats are used. Prior to vaccination the cats are bled on day 0 and approximately 2 ml serum is collected as pre-vaccination control. The prescribed dose of polypeptide preparation is injected intramuscularly into the lateral thigh muscles. The cats are vaccinated on days 0, 21, and 42 and bled on days 7, 14, 21, 28, 35, and 42, to obtain test sera.

Immunogenicity was determined by an ELISA measurement of anti-FeLV gp70 antibodies as follows: Immulon II microtiter plates (Dynatech) are coated with purified FeLV gp70 for 3 hr at 37° C. 50 ng protein per well in 100 μl coating buffer (0.1M $Na_2CO_3$, 0.02% $NaN_3$, pH 9.6) are used. Plates are then stored overnight at 4° C., and are stable for several weeks. Plates are washed 3X with ELISA wash (0.15 M NaCl, 0.15% Tween 20) and 100 μl experimental cat sera is diluted (usually 1:50) in buffer 3 (buffer 3=0.15 M NaCl, 0.001 M EDTA, 0.05 M Tris-HCl, pH 7.4, 0.05% Tween 20) was added to gp70 coated wells and incubated one hr at 37° C.

Plates are washed 3X with ELISA wash, then reacted 45 min at 37° C. with 100 μl/well of a 1:200 dilution in buffer 3 of rabbit anti-cat antibody conjugated to horseradish peroxidase.

Plates are washed 3X with ELISA wash, then reacted with 100 μl of substrate solution (5 ml 0.05 M citric acid, pH 4, +20μl 27.45 mg/ml ABTS+20 μl 2% $H_2O_2$ until signal to background color development is adequate. The reaction is stopped with 0.2 M HF and the optical density at 405 nm is determined.

Virus neutralizing antibody in cat sera is determined by a focus-forming assay as follows. Clone 81 cells contain a defective murine sarcoma virus genome. Upon infection of the cell with FeLV, the non-defective FeLV allows for expression of the sarcoma virus, and thus the appearance of a transformed cell phenotype. As transformed cells accumulate locally, a focus develops. The procedure used is from Fischinger, et al, *J Virol* (1974) 14:177–179. Tissue culture dishes are seeded on day −1 with $2\times10^5$ CCC clone 81 (S+L-) cells in 5 ml McCoYs 5A medium supplemented with 15% heat-inactivated fetal bovine serum and 50 μg/ml gentamycin. Dishes are incubated at 37° C. in a 5% $CO_2$ humidified incubator. On day 0 cells are treated with 1 ml DEAE-dextran (25 μg/ml in media) for one hr at 37° C. Cells are washed 1X with 2 ml media. Washed, treated cells are infected with a small volume (0.2–0.5 ml) of dilutions of the virus-containing stock in duplicate, for 60 min at 37° C., with intermittent rocking. Media (5 ml) is added to the dishes, and incubation continued at 37° C. The media is changed on day 1, day 4, day 8, and day 12. Foci are counted on days 10–14.

The presence of virus neutralizing antibodies is determined from the reduction in infectious virus titer upon incubation of a known amount of virus with cat serum, in the presence, or absence, of exogenous complement. The procedure is as follows. CCC clone 81 (S+L−) cells are seeded in 60 mm tissue culture dishes at $2\times10^5$ cells per dish in 5 ml media on day -1, and incubated at 37° C. in a 5% $CO_2$ humidified incubator. Serum samples are heat inactivated at 56° C. for 60 min. 100 μl Aliquots of the sera are serially diluted in media in quadruplicate. To all sample dilutions 100 μl of stock virus, diluted to contain 50–100 focus inducing units (FIU), are added. To duplicate wells of virus-antibody mixtures 50 μl of a 1:10 dilution of rabbit complement 1:50 final dilution, is added. These reactions are incubated 60 min at 37° C. The 81 cells are treated with 1 ml DEAE-dextran (25 μg/ml in media) for 60 min at 37° C., washed 1X with 2 ml media, then infected with the virus-antibody mixtures for 60 min at 37° C. with intermittent rocking. Media (5 ml) is added and the dishes are incubated at 37° C. for 10-14 days with media changes on day 1, day 4, day 8, and day 12. Foci are counted, and the neutralizing titer of the serum sample determined as the serum dilution which causes a 50% reduction of the input virus FIU titer.

Immunoprotection is measured by an ELISA assay for persistent viremia in FeLV challenged vaccinates. The procedure is as follows. Following the appearance of substantial anti-gp70 titers, the cats are challenged with a subcutaneous injection of $5 \times 10^6$ live FF 64/ST-FeSV transformed feline fibroblasts. Viremia is measured weekly by an ELISA that measures levels of FeLV core protein p27 by the use of several mouse monoclonal antibodies which recognize the protein. (Lutz, H., et al, supra).

Catching antibody (a pool of IgG fractions from several mouse monoclonal anti-p27 antibodies) was diluted to 5 μg/ml in coating buffer (0.1 M $Na_2CO_3$, 0.02% $NaN_3$, pH 9.6). Add 100 μl to each well of Immulon II microtiter plates (Dynatech) and incubate 3 hr at 37° C., then overnight at 4° C. Wash the coated plates 3X with ELISA wash (0.15 M NaCl, 0.05% Tween 20) and 1X with distilled water. Seal and store at −20° C. Samples are diluted 1:4 in buffer 3 containing 0.13% Tween 20. Add BSA to 0.1% after pH adjustment. Add 100 l of diluted sample to duplicate wells of the coated, washed plates. Include a standard curve of purified p27, 0-50 ng/well, in 100 μl of buffer 3+0.1% Tween 20. Incubate for 60 min at 37° C. Wash the plates 3X with ELISA wash. Dilute the conjugated antibody (a pool of two mouse anti-FeLV p27 antibodies conjugated to horseradish peroxidase) as determined for the particular conjugate, and add 100 μl to each well. Incubate 30-60 min at 37° C. Wash the plates 3X with ELISA wash. Add 100 μl substrate solution (5 ml 0.05 M citric acid, pH 4+20 μl 27.45 mg/ml ABTS+20 μl 2% $H_2O_2$ to each well, and incubate at room temperature until the signal to background ratio is adequate. Stop the reaction with 100 μl 0.2 M HF, and determine the optical density at 405 nm. The p27 concentration can be determined from the standard curve.

The protein products described in the examples may be evaluated for immunogenicity and immunoprotective activity by the above tests and shown to be effective vaccines against FeLV infection.

Guinea Pig Trials: Immunogenicity and Efficacy

Guinea pigs (350-400 g, 3 animals per group) were vaccinated as follows:

Day 0: vaccination—injected IM with 0.2 mg conjugate in complete Freund's adjuvant or 0.4 mg fusion protein in incomplete Freund's adjuvant Day 14: incremental boost—injected with 0.2 mg conjugate in incomplete Freund's adjuvant or 0.4 mg fusion protein in incomplete Freund's adjuvant Day 28: final boost—injected with "10 ml equivalent" inactivated virus prepared as follows. FF64/280 feline fibroblast cells infected with Snyder-Theilen (ST) FeLV were grown to confluent monolayer in standard medium (Modified Eagle's Medium, L15) plus 10% fetal calf serum (FCS). The FCS was then withdrawn and replaced with medium alone. Supernatant was collected after 24-48 h and concentrated approximately 200-fold by ultrafiltration. Formaldehyde to 0.6% by weight was added to inactivate the virus. Aliquots (0.05 ml) of concentrate were diluted and then prepared with incomplete Freund's adjuvant for use as final boosts.

Test sera are taken from the guinea pigs two weeks after each injection. Immunogenicity tests on the sera for antibodies to gp70 and peptides I, II, III, and IV were made using the ELISA procedure described above. Virus neutralizing tests were also made on the guinea pig sera using the focus forming assay described above as well as complement-dependent antibody mediated cytotoxicity (C'DAC) tests according to Terasaki, P. I., and McClelland, J. D., *Nature* (1964) 204:998-1000. The C'DAC test used rabbit complement and FL74 (FeLV infected) cat cells as target cells for serum antibody binding and complement cytotoxicity.

The results of these tests are tabulated below. Except where indicated otherwise results not in parentheses are on sera taken after the initial vaccination. Results in parentheses are on sera taken after the killed virus injection.

|  | Immunogenicity | | | | | | |
| Vaccine | pepI | pepII | pepIII | pepIV | gp70 | C'DAC | Virus Neutralization |
| --- | --- | --- | --- | --- | --- | --- | --- |
| Ava | nd | nd | − (−) | − (−) | + (++) | + (+) | − | (−) |
| t9:3-19 | nd | nd | + (+) | − (−) | + (++) | − (+) | + | (+) |
| Apa | nd | nd | + (+) | − (−) | + (++) | − (+) | + | (+) |
| pepI | ++ (nd) | + (nd) | nd | nd | + (nd) | nd | +/− | (+/−) |
| pepII | − (nd) | ++ (nd) | nd | nd | ++ (nd) | nd | + | (+/−) |
| pepIII | nd | nd | ++ (++) | − (−) | +/− (++) | − (+) | +/− | (+) |
| pepIV | nd | nd | − (nd) | ++ (nd) | + (nd) | nd | + | (+/−) | nd = not determined
+, ++ = significant antibody titer/cytotoxicity/virus neutralization
− = no significant titer/cytotoxicity/virus neutralization The results of the immunogenicity tests show that all the vaccines produce antibodies to gp70 and that the killed virus injection produces a significant increase in anti-gp70 response. (Controls, vaccinated with saline/adjuvant, and boosted with killed virus failed to show a large response after a single boost.) A correlative increase was observed in the complement-dependent cytotoxicity after the killed virus boost.

The polypeptides of the invention are used for active immunization of cats against FeLV. For such use the polypeptides will usually be formulated with pharmaceutically acceptable liquid vehicles for parenteral injection such as saline, Ringer's solution, dextrose solution, and Hank's solution. As used herein to describe such vehicles, the term "pharmaceutically acceptable" means that the vehicle is nontoxic, generally inert, and does not affect the functionality of the active ingredients adversely. Preferably the formulation will contain one or more adjuvants (compounds capable of potentiating the desired immune response) such as the commonly used water and oil emulsions (e.g., Freund's adjuvants), alum (potassium aluminum sulfate), aluminum hydroxide, calcium phosphate, and synthetic polynucleotides. The dose and dosage regimen used in the vaccinations may vary depending upon the age and weight of the animal, the mode of parenteral administration, and the presence of adjuvants in the formulation. Individual doses will usually be in the range of about 0.1 to 10 mg polypeptide. As indicated the vaccine injections are preferably used to prime the immune response and are followed by injection with killed virus or subinfectious amounts of live virus. The vaccination will typically be followed by booster inoculations periodically through the first year of life and beyond. As used herein the term "immunogenic amount" is intended to encompass such doses.

The vaccine may be administered by any parenteral route (intravenously, intraarterially, intraperitoneally, subcutaneously, intradermally, intramuscularly, or intrathecally). It will preferably be administered subcutaneously or intramuscularly.

Modifications of the above described modes for carrying the invention that are obvious to those of skill in the fields of protein chemistry, immunology, recombinant DNA technology, and/or veterinary medicine are intended to be within the scope of the following claims.

I claim:

1. A microbially produced polypeptide comprising an amino acid sequence that is homologous to at least a portion of the amino acid sequence of gp85 envelope protein of feline leukemia virus subgroup B that occurs in the 210–250 region and the 415–450 region of the FeLV gp85 protein, and is an immunogen that primes or elicits a humoral response in cats and is useful for immunizing cats against feline leukemia virus infection.

2. The polypeptide of claim 1 wherein the gp70 envelope protein is from feline leukemia virus strain GA or strain ST.

3. The polypeptide of claim 1 wherein the amino acid sequence is homologous to at least a substantial portion of at least one of the hydrophilic domains of the gp85 protein that occurs in the 210–250 region and in the 415–450 region.

4. The polypeptide of claim 1 wherein the portion of the amino acid sequence of gp85 envelope protein is
   (a) met gly pro asn leu val pro asp gln lys pro pro ser;
   (b) asp gln lys pro ser arg gln ser gln ile glu;
   (c) pro glu tyr val tyr thr his phe asp lys thr val arg leu; or
   (d) asp lys thr val arg leu arg arg glu pro ile ser leu.

5. The polypeptide of claim 4 wherein the amino acid sequence is repeated in the polypeptide.

6. An *E. coli* produced fusion protein comprising:
   (a) a trpLE′, fusion peptide sequence and
   (b) an amino acid seqeunce that is homologous to at least a portion of the amino acid sequence of gp85 envelope protein of feline leukemia virus subgroup B that occurs in the 210–250 region and the 415–450 region of the FeLV gp85 protein, said fusion protein being an immunogen that primes or elicits a humoral response in cats and is useful for immunizing cats.

7. The fusion protein of claim 6 wherein the gp85 envelope protein is from feline leukemia virus strain GA or strain ST.

8. The fusion protein of claim 6 wherein the amino acid sequence is homologous to a substantial portion of at least one of the hydrophilic domains of the gp85 protein that occurs in the 210–250 region and in the 415–450 region.

9. The fusion protein of claim 6 wherein the portion of the amino acid sequence of gp85 envelope protein is
   (a) met gly pro asn leu val leu pro asp gln lys pro pro ser;
   (b) asp gln lys pro ser arg gln ser gln ile glu;
   (c) pro glu tyr val tyr thr his phe asp lys thr val arg leu; or
   (d) asp lys thr val arg leu arg arg glu pro ile ser leu.

10. The fusion protein of claim 6 wherein the protein is the product of expression of the plasmid ptGAΔAvaI, ptGAΔApaI, or pt9:3–19.

11. A conjugate of:
   (a) a polypeptide having an amino acid sequence that is homologous to at least a substantial portion of at least one of the hydrophilic domains of the gp85 envelope protein of feline leukemia virus subgroup B that occurs in the 210–250 region and in the 415–450 region coupled to
   (b) a carrier protein.

12. The conjugate of claim 11 wherein the polypeptide comprises the amino acid sequence
   (a) H - cys asp lys thr val arg leu arg arg glu pro ile ser leu - OH;
   (b) H - cys pro glu tyr val tyr thr his phe asp lys thr val arg leu - OH;
   (c) H - cys met gly pro asn leu val leu pro asp gln lys pro pro ser - OH; or
   (d) H - asp gln lys pro pro ser arg glu ser gln ile glu cys ser - OH.

13. A polypeptide of the formula
   (a) H - cys asp lys thr val arg leu arg arg glu pro ile ser leu - OH;
   (b) H - cys pro glu tyr val tyr thr his phe asp lys thr val arg leu - OH;
   (c) H - cys met gly pro asn leu val leu pro asp gln lys pro pro ser - OH; or
   (d) H - asp gln lys pro pro ser arg glu ser gln ile glu cys ser - OH.

* * * * *

UNITED STATES PATENT AND TRADEMARK OFFICE
CERTIFICATE OF CORRECTION

PATENT NO. : 4,789,702

DATED : December 6, 1988

INVENTOR(S) : Jack H. Nunberg

It is certified that error appears in the above-identified patent and that said Letters Patent is hereby corrected as shown below:

Column 17, Claim 4, line 49, after "val" insert -- leu --.

Column 18, Claim 9, line 22, after "pro" insert -- pro --.

Signed and Sealed this

Twelfth Day of September, 1989

Attest:

DONALD J. QUIGG

Attesting Officer

Commissioner of Patents and Trademarks